(12) United States Patent
Lin et al.

(10) Patent No.: US 9,513,240 B2
(45) Date of Patent: Dec. 6, 2016

(54) MEMS-BASED CALORIMETER, FABRICATION, AND USE THEREOF

(71) Applicant: The Trustees of Columbia University in the City of New York, New York, NY (US)

(72) Inventors: Qiao Lin, New York, NY (US); Bin Wang, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 345 days.

(21) Appl. No.: 13/972,783

(22) Filed: Aug. 21, 2013

(65) Prior Publication Data

US 2014/0092935 A1   Apr. 3, 2014

Related U.S. Application Data

(63) Continuation-in-part of application No. PCT/US2012/026163, filed on Feb. 22, 2012, which is a continuation-in-part of application No. PCT/US2013/051910, filed on Jul. 24, 2013.

(60) Provisional application No. 61/445,414, filed on Feb. 22, 2011, provisional application No. 61/500,011, filed on Jun. 22, 2011, provisional application No. 61/506,509, filed on Jul. 11, 2011, provisional
(Continued)

(51) Int. Cl.
*G01N 25/00* (2006.01)
*G01N 25/48* (2006.01)

(52) U.S. Cl.
CPC .......... *G01N 25/48* (2013.01); *G01N 25/4893* (2013.01)

(58) Field of Classification Search
CPC .................................................. G01N 25/48
USPC .......... 374/10–12, 29–39, 179, 121; 422/51; 438/147
See application file for complete search history.

(56) References Cited

U.S. PATENT DOCUMENTS 3,071,495 A * 1/1963 Hanlein .................. H01L 35/34
 136/201
3,552,207 A  1/1971 Monk et al.
(Continued)

FOREIGN PATENT DOCUMENTS

JP 2001-165881 6/2001
JP 2001-349855 12/2001
(Continued)

OTHER PUBLICATIONS

Barnes et al., "A femtojoule calorimeter using micromechanical sensors", AIP: Review of Scientific Instruments, 65:3793-3798 (Dec. 1994).
(Continued)

*Primary Examiner* — Lisa Caputo
*Assistant Examiner* — Janice M Soto
(74) *Attorney, Agent, or Firm* — Baker Botts L.L.P.

(57) ABSTRACT

MEMS-based calorimeter including two microchambers supported in a thin film substrate is provided. The thin film substrate includes a thermoelectric sensor configured to measure temperature differential between the two microchambers, and also includes a thermally stable and high strength polymeric diaphragm. Methods for fabricating the MEMS-based calorimeter, as well as methods of using the calorimeter to measure thermal properties of materials, such as biomolecules, or thermodynamic properties of chemical reactions or physical interactions, are also provided.

44 Claims, 41 Drawing Sheets

Related U.S. Application Data application No. 61/506,514, filed on Jul. 11, 2011, provisional application No. 61/538,725, filed on Sep. 23, 2011, provisional application No. 61/538,729, filed on Sep. 23, 2011, provisional application No. 61/542,147, filed on Sep. 30, 2011, provisional application No. 61/542,651, filed on Oct. 3, 2011, provisional application No. 61/577,452, filed on Dec. 19, 2011, provisional application No. 61/675,025, filed on Jul. 24, 2012, provisional application No. 61/769,591, filed on Feb. 26, 2013.

(56) References Cited

U.S. PATENT DOCUMENTS

| | | | |
|---|---|---|---|
| 4,040,288 | A | 8/1977 | Kotelnikov et al. |
| 4,333,332 | A | 6/1982 | Privalov |
| 5,439,291 | A | 8/1995 | Reading |
| 5,813,763 | A * | 9/1998 | Plotnikov .......... G01N 25/4866 374/11 |
| 6,079,873 | A | 6/2000 | Cavicchi et al. |
| 6,185,232 | B1 * | 2/2001 | Hess, Jr. .............. H01S 5/0612 372/102 |
| 6,561,692 | B2 * | 5/2003 | Danley .................. G01K 17/00 374/1 |
| 6,988,826 | B2 | 1/2006 | Zibri et al. |
| 7,564,267 | B1 | 7/2009 | Patterson |
| 7,578,613 | B2 | 8/2009 | Reading |
| 2003/0106799 | A1 * | 6/2003 | Covington ........ B01L 3/502707 204/600 |
| 2004/0038426 | A1 | 2/2004 | Manalis |
| 2004/0180204 | A1 | 9/2004 | Zumbrunnen et al. |
| 2005/0254547 | A1 | 11/2005 | Zribi et al. |
| 2006/0187998 | A1 | 8/2006 | Danley |
| 2007/0286769 | A1 | 12/2007 | Vlassak et al. |
| 2011/0216804 | A1 | 9/2011 | Roukes et al. |

FOREIGN PATENT DOCUMENTS

| | | |
|---|---|---|
| WO | WO 98/16818 | 4/1998 |
| WO | WO 2009/059110 A1 | 5/2009 |
| WO | WO 2011/142518 A1 | 11/2011 |
| WO | WO 2012/116092 | 8/2012 |
| WO | WO 2014/018688 | 1/2014 |
| WO | WO 2014/197740 A1 | 12/2014 |

OTHER PUBLICATIONS

Cavicchi et al., "Micro-differential scanning calorimeter for combustible gas sensing", Sensors and Actuators B; Chemical, 97(1):22-30 (Jan. 2004).
Lai et al., "High-speed ($10^4$ ° C/s) scanning microcalorimetry with monolayer sensitivity ($J/m^2$)", Applied Physics Letters, 67:1229-1231 (Aug. 1995).
Vanden Poel et al., "Performance and calibration of the flash DSC1, a new, MEMS-based fast scanning calorimeter", Journal of Thermal Analysis and Calorimetry, 110(3):1533-1546 (Dec. 2012).
Wang et al., "A MEMS Isothermal Titration Biocalorimeter", 16th International Conference on Miniaturized Systems for Chemistry and Life Sciences, pp. 195-197 (Oct. 28-Nov. 1, 2012) Okinawa, Japan.
International Search Report and Written Opinion for PCT/US2014/041181,dated Oct. 9, 2014.
International Search Report and Written Opinion for PCT/US2012/026163, dated Jun. 29, 2012).
Allen, et al., "MEMS-Based Scanning Calorimeter for Thermodynamic Properties of Nanostructures", Microscale Thermophysical Engineering, 2:11-19 (1998).
Carpentier, et al., "Temperature-Modulated Differential Scanning Calorimetry as a Specific Heat Spectroscopy", Journal of Physics D: Applied Physics, 35(4): 402-408 (2002).
Craig, et al., "The Use of Modulated Temperature DSC for the Study of Pharmaceutical Systems: Potential Uses and Limitations", Pharmaceutical Research, 15(8):1152-1153 (1998).
Feire, "Differential Scanning Calorimetry", Methods in Molecular Biology, 40:191-218 (1995).
Finotello, et al., "AC Calorimetric Studies of Phase Transitions in Porous Substrates. Superfluid Helium and Liquid Crystals", Thermochimica Acta, 304-305:303-316 (1997).
Garden, et al., "Entropy Production in AC-Calorimetry", Thermochimica Acta, 461(1-2):57-66 (2007).
Gill, "Modulated Differential Scanning Calorimetry", Journal of Thermal Analysis, 40:931-939 (1993).
Gill, et al., Differential Scanning Calorimetry Techniques: Applications in Biology and Nanoscience:, Journal of Biomolecular Techniques, 21(4):167-193 (Dec. 2010) [retrieved Jun. 21, 2011].
Hinz, et al., "Measurement and Analysis of Results Obtained on Biological Substances with D.S.C.", Journal of Chemical Thermodynamics, 33:1511-1525 (2001).
Höhne, et al., "Differential Scanning Calorimetry", Springer, Table of Contents (2003).
Huth, et al., "Differential AC-Chip Calorimeter for Glass Transition Measurements in Ultrathin Films", Journal of Polymer Science Part B: Polymer Physics, 44(20):2996-3005 (Oct. 2006).
Inoue, et al., "AC-Calorimetry for Detecting Electronic Phase Transitions at Low Temperatures using Micro-Chip Devices", Thermochimica Acta, 492(1):85-88 (2009).
Jung, et al., "Peltier AC Calorimeter", Thermochimica Acta, 391:7-12 (2002).
Lee, et al., "High-Sensitivity Microfluidic Calorimeters for Biological and Chemical Applications", PNAS, 106(36):15225-15230 (Sep. 2009).
Lerchner, et al., "Chip Calorimetry and Its Use for Biochemical and Cell Biological Investigations", Chemical Engineering and Processing, 47:991-999 (2008).
Lortz, et al., "Modulated-Bath AC Calorimetry Using Modified Commercial Peltier-Elements", Review of Scientific Instruments, 76:103902 (20 pages) (2005).
Maggiolino, et al., "MEMS_DSC: A New Device for Microcalorimetric Analysis in the Biological Field", Microsystems Technologies, 16(6): 967-971 (Jun. 2010).
GE Healthcare Life Sciences, "MicroCal" http://www.gelifesciences.com/webapp/wcs/stores/servlet/catalog/en/GELifeSciences-uk/brands/microcal/# [Retrieved on Dec. 17, 2013].
Olson, et al., "The Design and Operation of a MEMS Differential Scanning Nanocalorimeter for High-Speed Heat Capacity Measurements of Ultrathin Films", Journal of Microelectromechanical Systems, 12(3):355-364 (Jun. 2003).
Plotnikov, et al., "A New Ultrasensitive Scanning Calorimeter", Analytical Biochemistry, 250(2):237-244 (1997).
Robertson, et al., "Protein Structure and the Energetics of Protein Stability", Chemical Reviews, 97:1251-1267 (1997).
Rowe, D.M., "CRC Handbook of Thermoelectrics", 1st Ed.: CRC-Press, Boca Raton, FL, Table of Contents (1995).
van Herwaarden, et al., "Overview of Calorimeter Chips for Various Applications", Thermochimica Acta, 432:192-201 (2005).
Wang, et al., "Demonstration of MEMS-Based Differential Scanning Calorimetry for Determining Theimodynamic Properties of Biomolecules", Sensors and Actuators B: Chemical, 134(2):953-958 (Sep. 2008).
Wang, et al., "A MEMS Differential Calorimeter for Bimolecular Characterization", 18th IEEE International Conference on Micro Electro Mechanical Systems, pp. 814-817 (Jan. 30-Feb. 3, 2005).
Wang, et al., "A MEMS Differential Scanning Calorimeter for Thermodynamic Characterization of Biomolecules", 24th International Conference on Micro Electro Mechanical Systems, pp. 821-824 (Jan. 2011).
Wang, et al., "A MEMS Thermal Biosensor for Metabolic Monitoring Applications", Journal of Microelectromechanical Systems, 17(2):318-327 (Apr. 2008).
Wunderlich, "Quasi-Isothermal Temperature-Modulated Differential Scanning Calorimetry (TMDSC) for the Separation of Reversible and Irreversible Thermodynamic Changes in Glass Transition

(56) References Cited

OTHER PUBLICATIONS and Melting Ranges of Flexible Macromolecules", *Pure and Applied Chemistry*, 81(10):1931-1952 (2009).

Youssef, et al., "MEMS Scanning Calorimeter with Serpentine-shaped Platinum Resistors for Characterization of Microsamples", *Journal of Microelectromechanical Systems*, 18(2):414-423 (Apr. 2009).

U.S. Appl. No. 14/603,848 (US 2015/0285751), filed Jan. 23, 2015 (Oct. 8, 2015).

JP Office Action dated Aug. 18, 2015 in JP Patent Application No. 2013-554690.

Supplementary European Search Report mailed Apr. 15, 2016 in EP Application No. 12748936.

Supplementary European Search Report dated Jun. 21, 2016 in EP Application No. 13822418.

* cited by examiner

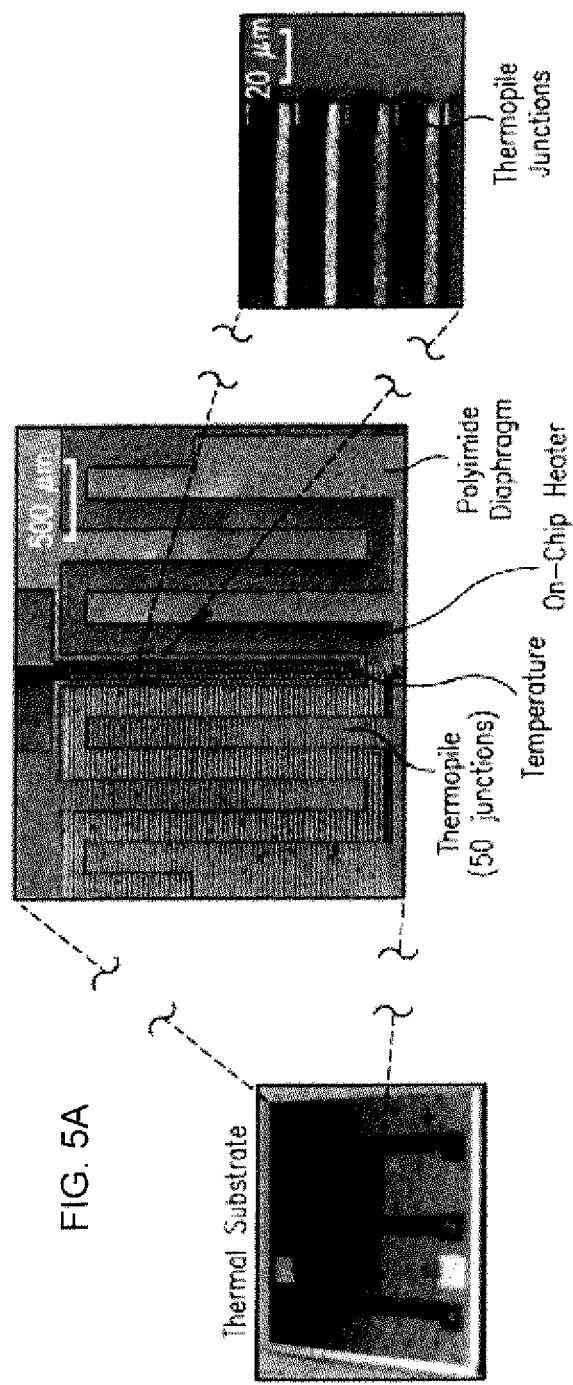
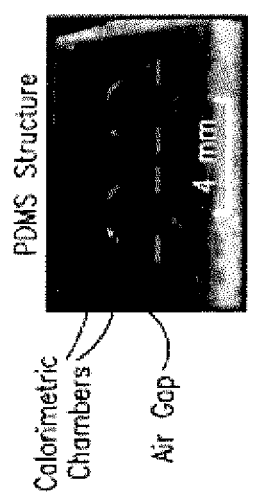
FIG. 5A
FIG. 5B
FIG. 5C
FIG. 5D

| | Temperature (°C) | Stoichiometry (N) | $K_B(M^{-1})$ | $\Delta H$ (kJ/mol) |
|---|---|---|---|---|
| Our results | 23 | 1.00 | ~6.0x10$^3$ | 30.0 |
| | 35 | 1.05 | ~2.8x10$^3$ | 27.8 |
| Published data* | 25 | 1.01 | 5.63x10$^3$ | 29.9 |
| | 40 | 0.97 | 3.17x10$^3$ | 29.4 |

*Data source: www.microcalorimetry.com

FIG. 33

| | Temperature (°C) | Stoichiometry (n) | K (M⁻¹) | ΔH (kJ/mol) |
|---|---|---|---|---|
| Our results | 23 | 1.01 | ~9.0×10⁴ | 52.3 |
| | 35 | 1.07 | ~4.0×10⁴ | 56 |
| Published data* | 28 | 1.00 | 8.27×10⁴ | 51.4 |
| | 38 | 1.04 | 4.85×10⁴ | 57.5 |

FIG. 35

MEMS-BASED CALORIMETER, FABRICATION, AND USE THEREOF

CROSS REFERENCES TO RELATED APPLICATIONS

This application is a continuation-in-part of PCT Application No. PCT/US2012/026163 filed Feb. 22, 2012, which claims priority from United States Provisional Application Nos. 61/445,414, filed Feb. 22, 2011; 61/500,011, filed Jun. 22, 2011; 61/506,509, filed Jul. 11, 2011; 61/506,514, filed Jul. 11, 2011; 61/538,725, filed Sep. 23, 2011; 61/538,729, filed Sep. 23, 2011; 61/542,147, filed Sep. 30, 2011; 61/542,651, filed Oct. 3, 2011; and 61/577,452, filed Dec. 19, 2011. This application is also a continuation-in-part of PCT Application No. PCT/US2013/051910 filed Jul. 24, 2013, which claimed priority from U.S. Provisional Application Nos. 61/675,025, filed Jul. 24, 2012, and 61/769,591, filed Feb. 26, 2013. The disclosure of each of these applications is incorporated by reference herein in its entirety.

STATEMENT REGARDING FEDERALLY FUNDED RESEARCH

This invention was made with government support under DBI-0650020 and CBET-0854030, both awarded by the National Science Foundation. The government has certain rights in this invention.

BACKGROUND

Differential scanning calorimetry (DSC) is a thermoanalytical technique that measures heat generated or required in thermally active processes as the temperature of a sample is varied. When applied to biochemical systems, DSC can provide a label-free method to determine the thermodynamic properties of a wide variety of biomolecular interactions and conformational transition. DSC instruments, however, can be cumbersome and require large sample consumption, which has hindered the widespread application of DSC to biomolecular characterization.

Microelectromechanical Systems (MEMS) are small integrated devices or systems that combine electrical and mechanical components in very small mechanical devices. MEMS technology is based on fabrication technologies that can realize miniaturization, multiplicity, and microelectronics.

Some currently available MEMS calorimeters provide solid- or gas-phase or droplet-based detections. However, it can be difficult to properly handle liquid samples in a well-defined environment in the currently available MEMS calorimeters.

Flow-through and continuous-flow MEMS calorimeters integrate microfluidic chambers or channels as biological reactors. These devices can provide controlled fluidic environments and can allow easy integration with other microfluidic functionalities or thermal sensing configurations for biochemical thermodynamic investigations. However, these devices can still require a large amount of samples while being limited by significant convective heat leakage due to the continuous flow.

In addition, calibrating existing MEMS DSC devices can be complicated due to a lack of integrated heating elements and temperature sensing. Temperature-modulated calorimetry (AC calorimetry) involves calorimetric measurements under small temporally periodic temperature variations. Such temperature modulation can allow thermal relaxation of biomolecules, and thus AC calorimetry can detect biomolecular interactions under quasi-equilibrium conditions, and allow the biochemical reaction signal to be extracted at the modulation frequency in the face of broad-band background noise. However, these chips can involve thin solid films and operating parameters which are not suitable for biomolecular characterization in solution phase.

Isothermal titration calorimetry (ITC) can measure heat generated or required for a biochemical reaction as a function of the molar reactant ratio, and has been used in applications such as drug discovery and biotherapeutic development. However, conventional ITC instruments can have complicated structural designs, slow thermal response, and large sample and reagent consumption.

SUMMARY

In accordance with one aspect of the disclosed subject matter, a microdevice is provided. The microdevice includes a first thermally isolated microchamber, a second thermally isolated microchamber, and a thin film substrate. The first and second microchambers can be a sample chamber and a reference chamber, respectively. The sample and reference chambers can be identical in volume and configuration, and arranged side by side, each supported on the thin film substrate. The thin film substrate can include a thermoelectric sensor located under each of the sample and reference chambers and configured to measure the temperature differential between the sample and reference chambers. The thin film substrate can also include a polymeric diaphragm made of a material having a glass transition temperature greater than 150° C. and thermal decomposition temperature greater than 250° C.

In some embodiments of the microdevice, the thermoelectric sensor includes a thermocouple having a thermoelectric sensitivity of greater than 80 μV/° C. In other embodiments, the thermoelectric sensor is configured as a thin-layer thermopile including a plurality of elongated segments of dissimilar materials, adjacent segments of dissimilar materials being joined together at opposite ends, thereby forming thermocouple junctions. For example, the dissimilar thermoelectric materials can include n-type and p-type bismuth telluride, and n-type and p-type antimony telluride. In one exemplary embodiment, the thermoelectric materials are antimony-bismuth (Sb—Bi).

The material of the polymeric diaphragm for the thin film substrate can have a tensile strength of greater than 55 MPa and Young's Modulus greater than 500 MPa. For example, the polymeric diaphragm can be made from a material such as but not limited to polyimide, parylene, polyester, and polytetrafluoroethylene. In one embodiment, the polymeric diaphragm is made from polyimide.

In certain embodiments, the thin film substrate of the microdevice can further include a first microheater and a first temperature sensor, each aligned under the first thermally isolated microchamber; and a second microheater and a second temperature sensor, each aligned under the second thermally isolated microchamber. In such embodiments, the thermocouple junctions of the thermoelectric sensor can be located near the center of each of the first and second thermally isolated microchambers, and vertically aligned with the first temperature sensor and the second temperature sensor, respectively. The microheaters and the temperature sensors can be in a form of a thin layer of deposited metal/alloy or metals/alloys impregnated in the thin film substrate. The microheaters can be patterned to provide uniform heating for the microchambers.

In some embodiments, the chambers of the microdevice are defined by a surrounding wall made from polydimethylsiloxane (PDMS). The thin film substrate of the microdevice can include a top layer made from a mixture of PDMS and the material from which the polymeric diaphragm is made.

In some embodiments, the microdevice further includes a first introduction channel and a second introduction channel. Each of the first introduction channel and a second introduction channel can be configured to provide passive chaotic mixing for a solution flowing through the introduction channel. For example, the first and/or the second introduction channel can include a portion having a serpentine shape, and can further include internal ridges sufficient for creating turbulence in the solution flowing through the first or the second introduction channel.

In accordance with another aspect of the disclosed subject matter, a method of determining a thermal property of an analyte is provided. A sample material containing an analyte is provided in the sample chamber, and a reference material not containing the analyte is provided in the reference chamber. A thermal enclosure enclosing the microdevice is heated at a predetermined temperature scanning rate. A thermal property of the analyte can be determined based on the measured temperature differential between the sample chamber and reference chamber.

In some embodiments of the method, a temporally periodic variation in the heating power can be provided during the heating of the thermally isolating enclosure. Providing the temporally periodic variation in the heating power can be performed using the microheaters of the microdevice for temporally modulated heating. The temporal modulation of the heating can be controlled by a waveform generator.

In accordance with another aspect of the disclosed subject matter, a method of determining heat involved in a reaction between at least two substances is disclosed. A sample solution containing a mixture of a first substance and a second substance is provided in the sample chamber, a reference solution is provided in the reference chamber. A thermal enclosure enclosing the microdevice is maintained at a constant temperature. The heat involved in the reaction between the first substance and the second substance at the given temperature can be determined based on the measured temperature differential between the sample chamber and reference chamber.

The reaction between the first and second substances can be a chemical reaction or a physical binding system, for example, ligand-protein binding. The thermal enclosure temperature can be varied such that the heat involved in the reaction can be determined at different temperature. Likewise, the concentration ratio between the two substances can also be varied such that reaction stoichiometry can be determined by the heat measured at different concentration ratios. The sample and/or reference solution can be fed into the respective chambers through an introduction channel as described above, which can provide passive mixing.

In an exemplary embodiment, a microelectromechanical systems-based calorimetric device for characterization of biomolecular interactions includes a first micromixer, a second micromixer, a thermally-isolated reaction chamber, a thermally-isolated reference chamber, and a thermoelectric sensor. The thermally-isolated reaction chamber is in fluid contact with the first micromixer. The thermally-isolated reference chamber is in fluid contact with the second micromixer. The thermoelectric sensor is configured to measure at least one temperature metric associated with reaction chamber and the reference chamber.

The first and second micromixers can be passive chaotic micromixers. For example, the first and second micromixers can be formed from a serpentine channel with herringbone shaped ridges on the ceiling thereof. The device can further include a first inlet a second inlet in fluid contact with the first micromixer, and a third inlet and a fourth inlet in fluid contact with the second micromixer.

The reaction chamber and reference chamber can be microchambers such as polydimethylsiloxane microchambers. The reaction chamber and reference chamber can be serpentine chambers. The reaction chamber and reference chamber can be disposed on a diaphragm such as a polyimide diaphragm that serves as a base for the reaction chamber and the reference chamber.

In accordance with an exemplary embodiment of the disclosed subject matter, the thermoelectric sensor can be a thermopile. The thermopile can be, for example, an antimony-bismuth thermopile. A first thermopile junction can be located on a first side of the reaction chamber, while a second thermopile can be located on the first side of the reference chamber.

The reaction chamber and reference chamber can be surrounded by an air cavity. In accordance with an exemplary embodiment of the disclosed subject matter, the air cavity can include a serpentine channel. The device can further include a temperature sensor and a heater for the reaction chamber and the reference chamber.

In accordance with an exemplary embodiment of the disclosed subject matter, the at least one temperature metric can be a differential temperature between the reaction chamber and the reference chamber. In other embodiments, the at least one temperature metric can be a temperature of the reaction chamber and a temperature of the reference chamber.

The disclosed subject matter further provides microelectromechanical systems-based methods for characterization of a biomolecular interaction between a first solution and a second solution. In one example, a method includes mixing the first solution and the second solution to form a reaction solution, mixing the first solution and a buffer solution to form a reference solution, and measuring a differential temperature between a reaction chamber containing the reaction solution and a reference chamber containing the reference solution. The differential temperature can be measured using a thermoelectric sensor such as a thermopile on the microelectromechanical systems-based device.

In accordance with an exemplary embodiment of the disclosed subject matter, micromixers on the microelectromechanical systems-based device (e.g., passive chaotic micromixers) can be used to mix the first and second solutions.

The method can further include computing a differential power based at least in part on the differential temperature. At least one thermodynamic reaction parameter can be calculated based at least in part on the differential power. The thermodynamic reaction parameter can be, for example, an equilibrium binding constant, a stiochiometry, or a molar enthalpy change.

A baseline temperature differential between the reaction chamber and the reference chamber can be measured prior to the introduction of the reaction solution and the reference solution. The baseline temperature differential can then be subtracted from the differential temperature for error correction. The device can also be calibrated using an on-chip heater.

The disclosed subject matter further provides microelectromechanical systems-based calorimetric devices for characterization of biomolecular reactions. In an exemplary embodiment, a device includes first mixing means for mixing a first solution and a second solution, second mixing means for mixing the first solution and a buffer solution, a thermally-isolated reaction chamber in fluid contact with the first mixing means, a thermally-isolated reference chamber in fluid contact with the second mixing means, and detection means for measuring a differential temperature between the reaction chamber and the reference chamber. The device can further include computing means for computing a differential power based at least in part on the differential temperature, and calculating means for calculating at least one thermodynamic reaction parameter based at least in part on the differential power.

BRIEF DESCRIPTION OF THE DRAWINGS

FIG. 5 Are images of a microdevice fabricated according to one embodiment of the disclosed subject matter: (a) the PDMS housing structure and air gap; (b) the solid substrate; (c) the thermopile, integrated microheater and temperature sensor embedded in the thin film substrate; and (d) the thermopile junctions.

FIG. 33 shows a comparison between reaction parameters obtained in accordance with an embodiment of the disclosed subject matter and published data reflecting reaction parameters obtained using commercial calorimeters.

FIG. 35 shows a second comparison between reaction parameters obtained in accordance with an embodiment of the disclosed subject matter and published data reflecting reaction parameters obtained using commercial calorimeters.

DETAILED DESCRIPTION

In accordance with one aspect of the disclosed subject matter, a microdevice is provided. The microdevice includes a first thermally isolated microchamber, a second thermally isolated microchamber, and a thin film substrate. The first and second microchambers are also referred herein as the sample chamber and reference chamber, respectively. The sample and reference chambers can be identical in volume and configuration, and arranged side by side. In accordance with an exemplary embodiment of the disclosed subject matter, the sample and reference chambers can have a circular configuration. However, a wide variety of geometric configurations can be used in accordance with the disclosed subject matter. The sample and reference chambers can each be supported on the thin film substrate. The thin film substrate can include a thermoelectric sensor located under each of the sample and reference chambers and configured to measure the temperature differential between the sample and reference chambers.

Figure 1A:
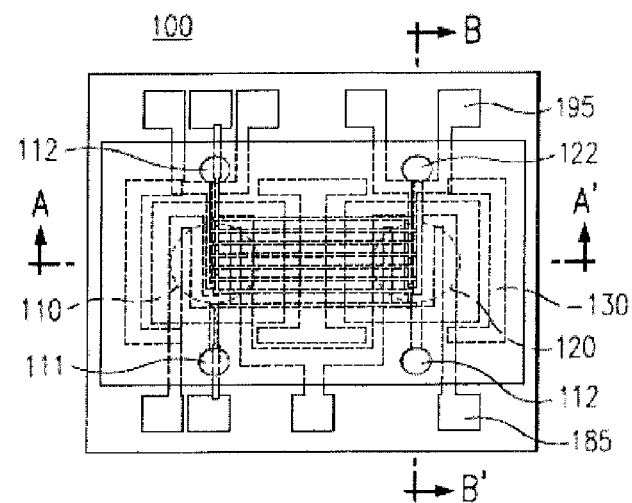
FIGS. 1a-1c depict a schematic of a microdevice according to some embodiments of the disclosed subject matter, in top (1a), isometric (1b), and sectional (1c) views.
Figure 1B:
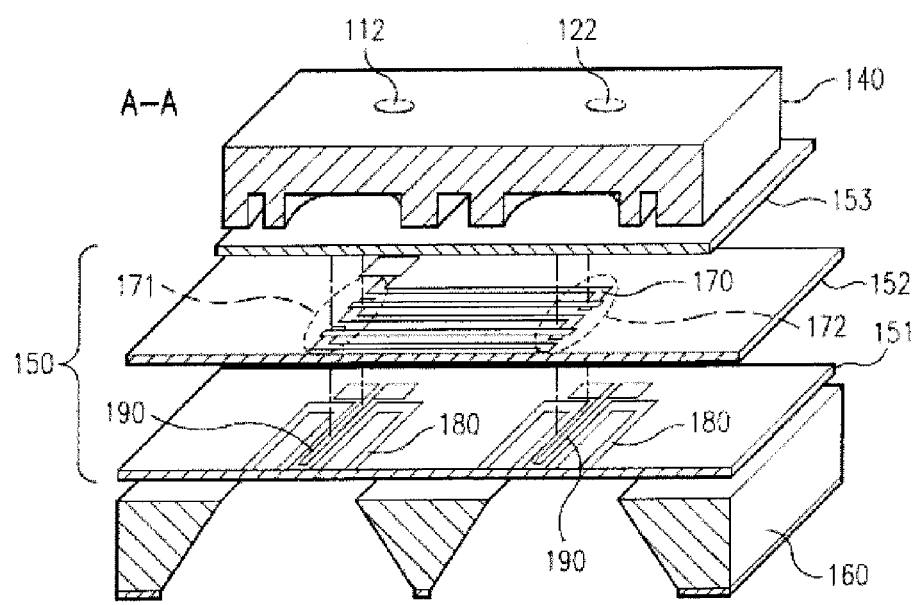
Figure 1C:
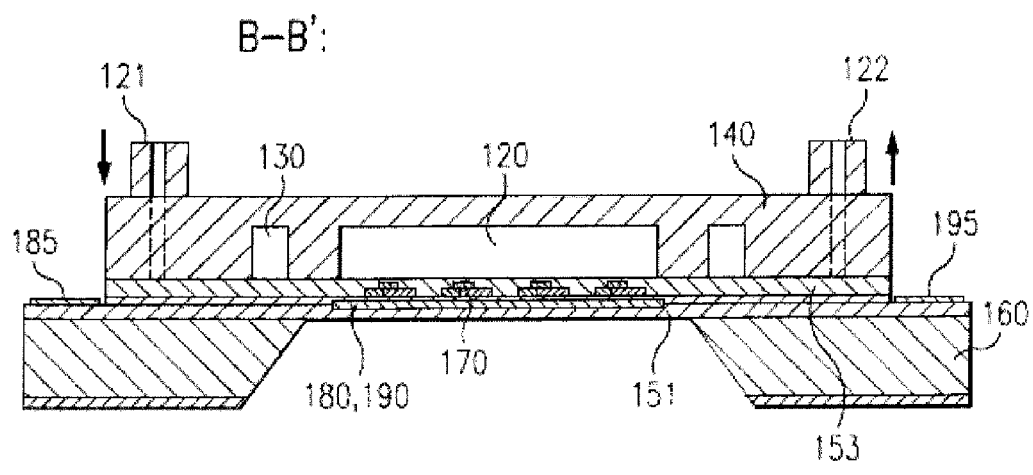

FIGS. 1a-1c depict an illustrative embodiment of the microdevice of the disclosed subject matter. The microdevice is also referred to as MEMS DSC device herein. The microdevice 100 includes two identical microchambers 110 and 120, which can hold sample and reference materials for calorimetric measurements. For easy reference, these microchambers are also referred to herein as the sample chamber and reference chamber, respectively, and collectively, "calorimetric chambers," or simply "chambers" Each of the sample and reference chambers is connected to an inlet port (111, 121) and an outlet port (112, 122) by microfluidic channels. The material for the housing of the chambers (140) can be made of any material suitable for microfabrication and thermal isolation. In certain embodiments, Polydimethylsiloxane (PDMS) is selected as the material to fabricate the calorimetric chambers for its ease of fabrication and packaging as well as biocompatibility. However, other materials suitable for microfabrication and thermal isolation can be used without departing from the scope of the disclosed subject matter. For example, a material having sufficient thermal stability within the temperature range of interest (e.g., −10° C. to 90° C.), reasonably strong bonding with the substrate surface, and minimized adsorption of macromolecules (e.g., proteins) can be used, The microchambers can be formed from polymers such as SU-8, parylene, polycarbonate, and polyether ether ketone (PEEK).

Each of the microchambers can be thermally isolated. For example, the air cavities (130) in FIG. 1a provide thermal isolation for the chambers. Air cavities can be formed from the same material used for fabrication of the microchambers. In accordance with an exemplary embodiment of the disclosed subject matter, the air cavities (130) can be formed from polydimethylsiloxane. However, other thermal isolation techniques can also be used as known in the art. For example, the microchambers can be thermally isolated by residing on a freestanding structure constructed from materials such as a polymeric material having low thermal conductivity. In order to further isolate the microchambers from the ambient environment, the microdevice 100 can be enclosed by a thermal enclosure (e.g., the microdevice 100 can be placed in a vacuum to minimize thermal energy dissipation to the ambient environment).

As shown in FIG. 1b, the microchambers (110, 120) are supported on a thin film substrate (150). The thin film substrate (150) along with air cavities (130) surrounding the chambers, provide thermal isolation that enables sensitive calorimetric measurements. The thin film (150) can include multiple polymeric layers or diaphragms (151, 152, 153). The layers 151, 152, 153 are integrated as shown in FIG. 1c, but for purpose of illustration, are shown in FIG. 1b as separate layers. Both of layers 151 and 152 can be made from a material have good thermal isolation property, as well as thermal and mechanical stability to withstand the thermal cycles required by repeated calorimetric measurements. In particular embodiments, the polymeric diaphragm can be made of a material having a glass transition temperature greater than 150° C. and thermal decomposition temperature greater than 250° C. For example, the material can be polyimide, parylene, polyester, SU-8, PDMS, and polytetrafluoroethylene, etc. The polymeric diaphragm can have a tensile strength of greater than 55 MPa, and/or Young's Modulus greater than 500 MPa. In particular embodiments, polyimide is selected as the diaphragm material because of to its excellent mechanical stiffness (Young's modulus: 2.5 GPa) and thermal stability (glass transition temperature: 285° C.).

To improve the adhesion between the housing material and the thin film substrate, an interfacing layer 153 can be made from a mixture of the material for layer 151 and/or 152, e.g., a mixture of polyimide/PDMS. The thin film substrate can be supported on another solid substrate (160), e.g., a silicon wafer. To improve thermal isolation, the solid substrate in the area underneath the bottom side of the thin film substrate corresponding to a cross section of each of the chambers can be removed, such that the portion of the thin film substrate under each of the chambers does not contact the solid substrate (i.e., it only contacts air, which is believed the best thermal insulator).

The microdevice can further include a thermoelectric sensor. A thermoelectric sensor can be coated on, embedded, or otherwise included in the thin film substrate and configured to measure the temperature differential between the two chambers. For example, a thin layer of thermopile (170) can be included between the polymeric layers (152, 153). As illustrated in FIGS. 1b and 1c, the thermopile can include a plurality of elongated segments of dissimilar materials, where adjacent segments of dissimilar materials are joined together at opposite ends, thereby forming thermocouple junctions (171 and 172). The thermocouple junctions underneath each chamber can be aligned to the central axis of each chamber. The material for the thermopile can include a variety of dissimilar pairs of metals, e.g., antimony-bismuth (Sb—Bi), or other pairs of materials providing high thermoelectric efficiency, such as n-type and p-type bismuth telluride, and n-type and p-type antimony telluride. For example, the thermoelectric sensor can have a thermoelectric sensitivity of greater than 80 µV/° C. per thermocouple. In particular embodiments, antimony (Seebeck coefficient: 43 µV/K) and bismuth (Seebeck coefficient: −79 µV/K) are selected for the thermopile material due to their high thermoelectric sensitivities and ease of fabrication. A wide variety of metals, semiconductors, and their compounds, including chrome, nickel, bismuth, antimony, bismuth telluride, and antimony telluride, can be used in fabricating the thermopile.

In accordance with another embodiment of the disclosed subject matter, the thermoelectric sensor can include a sample chamber thermoelectric sensor and a reference chamber thermoelectric sensor, each of which measures the absolute temperature of the reaction in the respective microchambers. The differential temperature can then be determined by calculating the different between the temperatures measured by the thermoelectric sensors. The thin film substrate can further include two sets of microheaters (180) and temperature sensors (190) which are aligned underneath the two chambers (110, 120), respectively. For example, the microdevice 100 can include an integrated tin-film resistive micro-temperature sensor and heater. The temperature sensors (190) can monitor the chamber temperatures in real time, and the microheaters (180) can provide heating to the chambers to generate a constant differential power for calorimetric calibration. For purposes of calibration, Joule heating can be generated by passing an electrical current through the microheater. The local temperature can then be determined by the temperature sensor based on a calibrated relationship between the temperature and the electrical resistance.

Both of the microheaters (180) and temperature sensors (190) can be embedded in the thin film, but vertically away and insulated from the thermopile (170). For example, the microheaters (180) and temperature sensors (190) can be embedded between layers 151 and 152. The contact pad (195) for the temperature sensor and the contact pad for the microheaters (185) can extend outside of the chamber housing structure for external electrical connection. Although shown in FIGS. 1b and 1c as situated on the same layer, the microheaters (180) and the temperature sensors (190) can also be situated on different layers. For precise temperature sensing, particularly in device calibration, the thermopile junctions (171, 172) can be aligned with the temperature sensors (190). The microheaters (180) can be patterned in a way to provide uniform heating of the chambers, for example, in a meandering pattern underneath the bottom area of the chambers. The material of the microheaters can be chosen from a variety of metals or metal alloys, for example, chromium/gold (Cr/Au).

Figure 2A:
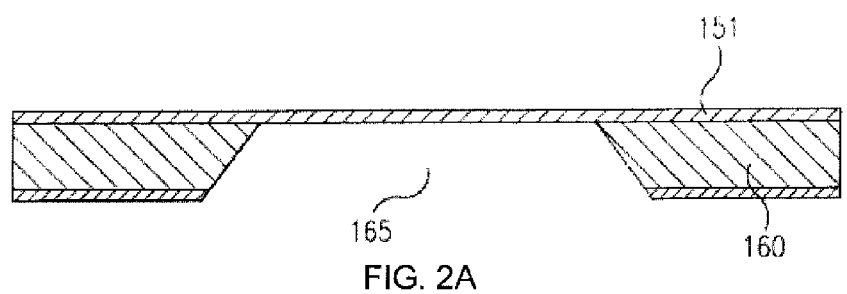
FIGS. 2a-2e depict a procedure for the fabrication of the microdevice according to some embodiments of the disclosed subject matter.
Figure 2B:
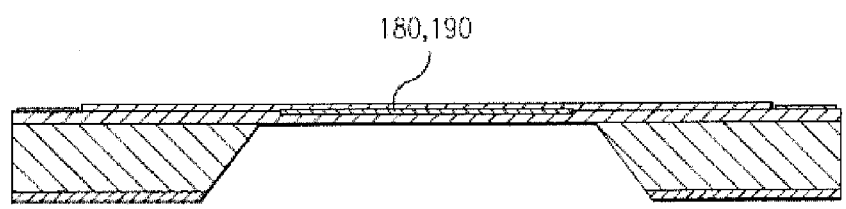
Figure 2C:
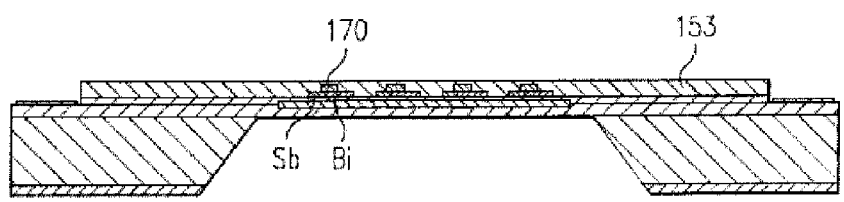
Figure 2D:
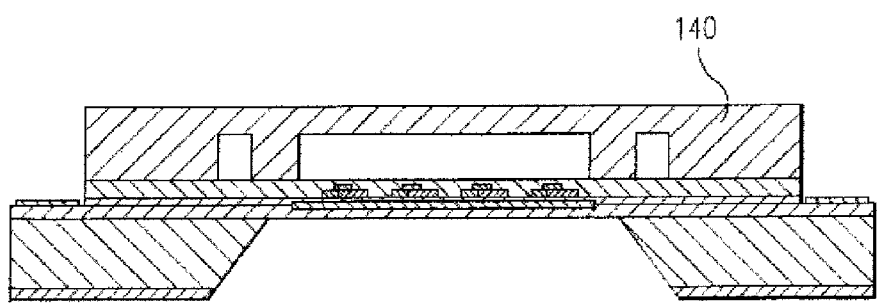
Figure 2E:
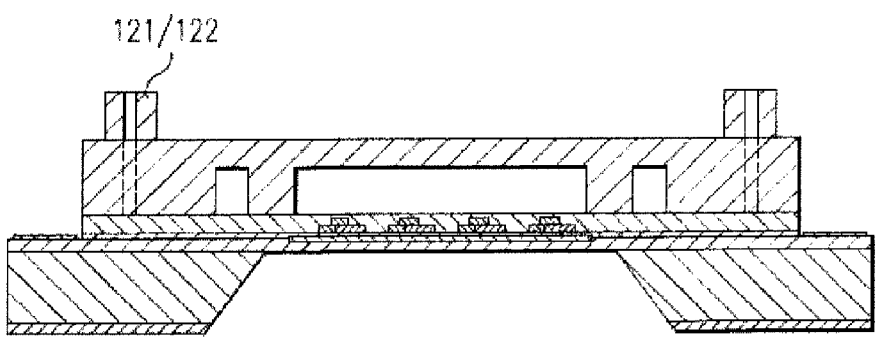

In one embodiment, the microdevice illustrated in FIGS. 1a-c can be fabricated by a procedure as outlined below. A solid substrate (160), such as silicon wafer, is provided. A polymeric diaphragm (151), e.g., a polyimide film, can be coated on the solid substrate, e.g., by spin-coating (FIG. 2a). A pair of cavities (165) can be etched using, for example, tetramethylammonium hydroxide (TMAH) into the backside of the solid substrate in the areas that correspond to the calorimetric chambers. After the curing of the polymeric diaphragm, microheaters (180) and temperature sensors (190) can be deposited by thermal evaporation of a metal or metal alloy, e.g., Cr/Au. This is followed by coating another polymeric diaphragm (152) on top of the microheaters and temperature sensors (FIG. 2b). Subsequently, the thermoelectric sensor (170), e.g., a thermopile, can be thermally evaporated and patterned using a standard lift-off process, and the thermoelectric sensor is further coated by another polymeric layer (153), e.g., a layer containing polyimide-PDMS mixture (FIG. 2c). The chamber housing structure (140) can then be fabricated, e.g., from PDMS using micromolding techniques on top of the thin film substrate, thereby forming the calorimetric chambers (FIG. 2d). Microfluidic structure such as microchannels connecting the chambers to the inlet and outlet ports (121/122) can also be fabricated (FIG. 2e). The residual silicon layer on the backside of the thin film can then be removed (FIG. 2e), thereby forming the freestanding thin film substrate portions under each of the chambers.

Figure 27:
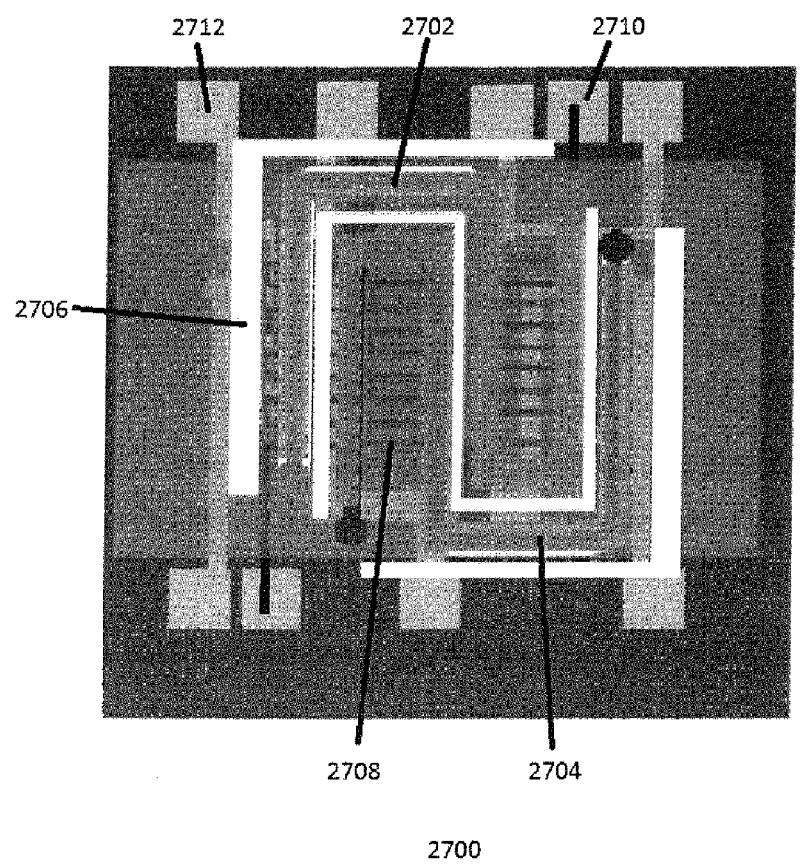
FIG. 27 depicts a top view of a schematic of a microdevice in accordance with an exemplary embodiment of the disclosed subject matter.

With reference to FIG. 27, a second embodiment of the microdevice in accordance with the disclosed subject matter is shown. The device 2700 includes a serpentine reference chamber (2702) and a serpentine sample chamber (2704). The reference chamber (2702) and sample chamber (2704) are thermally isolated by air cavities (2706). The microdevice 2700 also include a thermopile (2708). The use of serpentine microchambers (2702, 2704) can allow for a greater number of thermopile junctions can improve thermal isolation.

The microdevice 2700 also includes one or more contact pads (2710, 2712). The contact pads can provide an interface between the device and various electronic circuits. For example, contact pad 2710 can be coupled to the thermopile (2708). The adhesion between the ends of the thermopile (2708) and contact pad 2710 can be enhanced by surface roughening or chemical modification. A designed external packaging via a flip chip bonding method can also be implemented. The output of the thermopile (2708) is a voltage indicative of a differential temperature between the reference chamber (2702) and the sample chamber (2704). The contact pad 2710 can also be coupled to an electronic circuit for measuring and analyzing the output voltage. The term "coupled," as used herein, includes direct coupling such as direct electrical contact (e.g., through a soldered wire or alligator clip) as well as indirect coupling, as through wireless communication.

Figure 28:
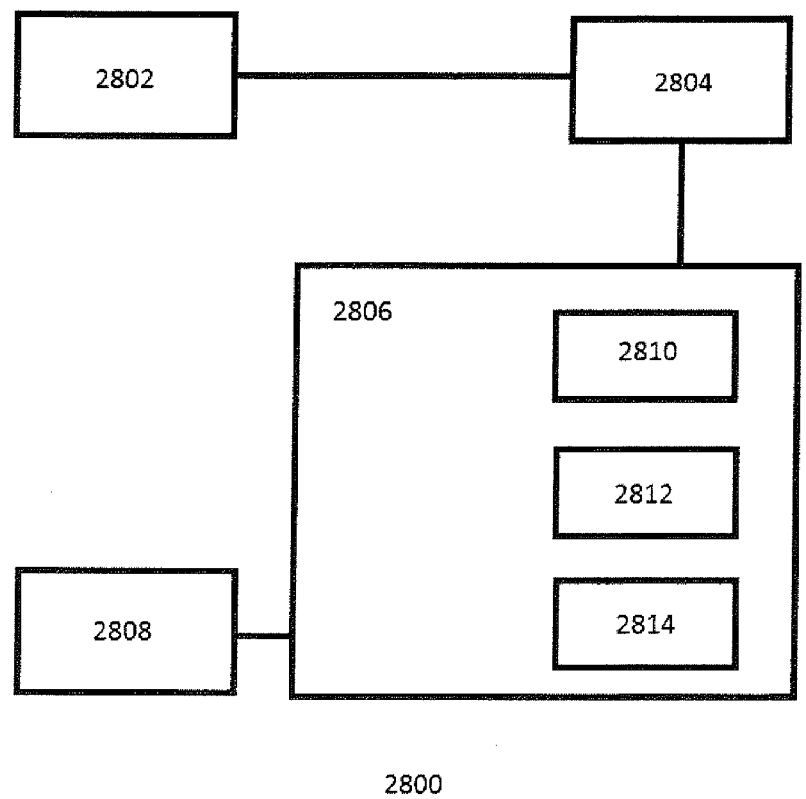
FIG. 28 is a diagram illustrating an electronic circuit that can be coupled to a microdevice in accordance with an exemplary embodiment of the disclosed subject matter.

An exemplary embodiment of an electronic circuit that can be coupled to contact pad 2710 in accordance with the disclosed subject matter is illustrated in FIG. 28. The contact pad (2802) acts as the interface between the microdevice and the one or more electronic circuits 2800. The contact pad can be coupled to a voltmeter (2804). The term "voltmeter," as used herein, is intended to encompass any instrument tat can be used to measure voltage, either directly or indirectly, including voltmeters and multimeters. The voltmeter (2804) can include at least one processor.

The voltmeter (2804) can be coupled to a calculation device (2806). The calculation device (2806) includes one or more processors formed by one or more electronic circuits. The calculation device (2806) can be coupled to a storage device (2808).

The calculation device (2806), as well as each of the components thereof, can be implemented in a variety of ways as known in the art. For example, each of the components of the calculation device can be implemented using a single integrated processor. In another embodiment, each component can be implemented on a separate processor. One or more components of the calculation device (2806) can be combined with the voltmeter (2804) rather than being a separate device.

The at least one processor can include one or more electronic circuits. The one or more electronic circuits can be designed so as to implement the disclosed subject matter using hardware only. Alternatively, the processor can be designed to carry out instructions specified by computer code stored in the storage device (2808). The storage device can be a hard drive, a removable storage medium, or any other non-transitory storage media. Such non-transitory storage media can store instructions that, upon execution, cause the at least one processor to perform the methods disclosed herein.

The calculation device (2806) can include a number of components, including an adjustment component (2810) for adjusting the output voltage based on a baseline in output voltage, a thermal power differential component (2812) for determining a thermal power differential based on the output voltage, and a reaction characterization component (2814) for calculating thermodynamic reaction parameters based on the thermal power differential.

With further reference to FIG. 27, contact pad 2712 can be coupled to a microheater and/or a temperature sensor. Contact pad 2712 can further be coupled to one or more electronic circuit for implementing the in-situ temperature monitoring and on-chip device calibration methods as disclosed herein.

In accordance with another aspect of the disclosed subject matter, a method of determining a thermal property of an analyte is provided. The method includes providing a microdevice as described above, providing a thermal enclosure enclosing the microdevice; loading a sample material containing an analyte into the first microchamber; loading a reference material into the second microchamber, the reference material does not contain the analyte; heating the thermal enclosure at a predetermined temperature scanning rate; and determining a thermal property of the analyte based on the measured temperature differential between the first microchamber and the second microchamber. The microdevice and the method of using the microdevice for calorimetric measurement are further described in conjunction with each other in the Examples below. It is appreciated that the microdevice including any of the specific features described below can be used in the method of using the microdevice, and vise versa.

Figure 3:
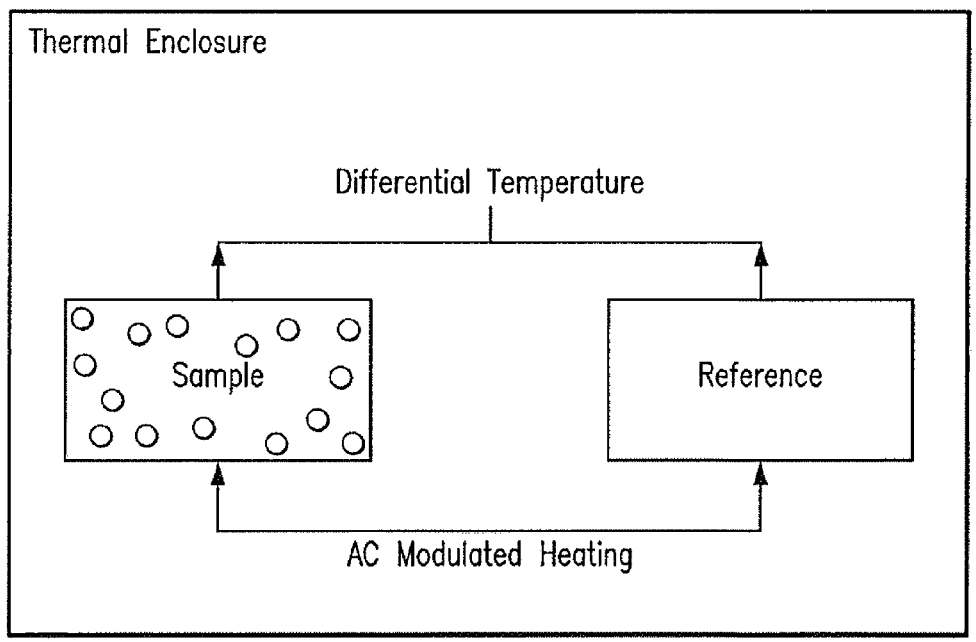
FIG. 3 is a schematic diagram illustrating the principle of AC differential scanning calorimetry according to the disclosed subject matter.

In some embodiments of the above method, a temporally periodic variation, or AC modulated heating, can be introduced to the reference and sample materials during the heating of the thermal enclosure, as illustrated in FIG. 3. This can lead to temperature modulation, which allows thermal relaxation of biomolecules, as well as allow the biochemical reaction signal to be readily extracted at the modulation frequency in the broad-band background noise. The temperature modulation can be achieved by using the microheaters included in the thin film substrate of the microdevice, controlled by a wave generator which can provide different frequency, magnitude, and other parameters for the on-chip heating.

In accordance with another aspect of the disclosed subject matter, a method of determining heat involved in a reaction between at least two substances is provided. The method includes: providing a MEMS device as described above; providing a thermal enclosure enclosing the microdevice; feeding a sample solution into the first thermally isolated microchamber, wherein the sample solution is prepared by mixing a first substance with a second substance; feeding a reference solution into the second thermally isolated microchamber, the reference solution does not contain at least one of the first and the second substances; and determining the heat involved in the reaction between the first substance and the second substance based on the measured temperature differential between the sample chamber and the reference chamber. During the measurement, the temperature of the thermal enclosure (that encloses the microdevice) can be maintained at a constant value. Thus, the method is also referred to as isothermal titration calorimetry (ITC). The reaction between the first and second substances can be a chemical reaction or physical binding. Thus, the two substances can be any of the variety of chemicals, biomolecules or other molecules that are reactive to each other, receptor-ligand, protein-enzyme, acid-base, etc., wherein the reaction between the two substances either generate, or absorb measurable heat.

Figure 29:
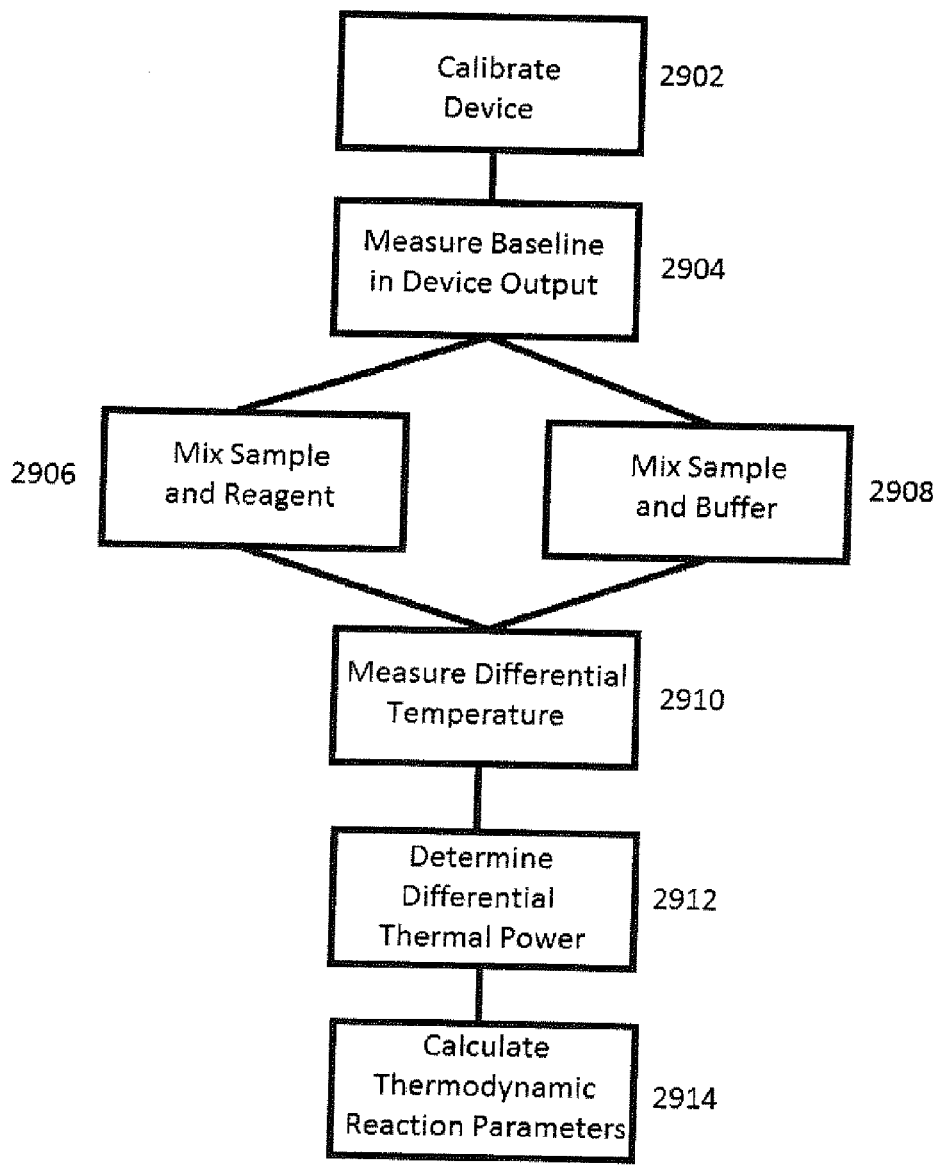
FIG. 29 is a flowchart illustrating a method for measuring a differential temperature and characterizing a reaction in accordance with an exemplary embodiment of the disclosed subject matter.

An exemplary method for measuring a differential temperature and characterizing a reaction in accordance with an embodiment of the disclosed subject matter is shown in FIG. 29. The method can include calibrating the device, measuring a baseline in device output, mixing the sample and the reactant, mixing the sample and the buffer, measuring a differential temperature, determining the thermal power, and calculating the thermodynamic reaction parameters.

To begin, the calorimetric device can be calibrated at 2902. For example, calibration techniques known in the art are described in A MEMS Differential-Scanning-calorimetric Sensor for Thermodynamic Characterization of Biomolecules by Bin Wang and Qiao Lin, J. Microelectromechanical Systems 21:5, 1165-1171 (October 2012), which is incorporated by reference herein in its entirety for all purposes.

The baseline in device output can then be measured at 2904. For example, if a thermopile is used to measure the differential temperature, the thermopile output voltage in the absence of a reaction can be measured. This can be accomplished by introducing a mixture of sample and buffer solutions into each of the chambers. The baseline in device output can then be stored in storage device 2808 as shown in FIG. 28 for future use.

A sample and a reactant can then be mixed at 2906. The sample and a buffer can be mixed substantially simultaneously at 2908. Mixing can be accomplished using a passive chaotic mixer such as the one illustrated in FIG. 4a. Using the device 400, the sample can introduced into inlet 431 and the reactant can be introduced into inlet 432. The sample and a buffer can be introduced in corresponding inlets to introduction channel 440. The sample and the reactant are passively mixed in introduction channel 430 and deposited into the sample chamber 410. The sample and the buffer are passively mixed in introduction channel 440 and deposited into the reference chamber 420. Titration techniques known in the art for use with Isothermal Titration calorimetry (ITC) can be used.

In accordance with an embodiment of the disclosed subject matter, titration on the MEMS device can be performed with a series of discrete reactions, with each reaction having a specific molar ratio of the reactants. Liquid cartridge segments can be used for introduction of reactants. For example, binding reagents in different concentrations can be prepared while the sample is prepared in a fixed concentration. As such, the molar ratio can be varied with the volume of sample and binding reagent maintained identical (e.g., 0.5 μL). The sample and binding reagent can each be loaded in a long access tubing sequentially separated by air (such that the molar ratio changes along with the sequence of reactant segments). The access tubes can be driven by a multi-port syringe pump. A each molar ratio, the syringe pump can deliver the exact amount of sample and reagent into the reaction chamber for heat measurement, as well as sample and buffer into the reference chamber. Buffer segments can also be added between two reactant segments in the sequence for purposes of cleaning the chamber or mixer.

With further reference to FIG. 29, the differential temperature of the reactions is measured at 2910. The measurement can be accomplished using a thermoelectric sensor such as a thermopile. The thermopile can output a voltage indicative of the differential temperature. The output voltage can then be adjusted based on the baseline in device output measured at 2904.

The differential temperature can then be used to determine a thermal power related to the reaction at 2912. The thermal power difference ΔP can be calculated as:

$$\Delta P = \frac{\Delta U}{S} \quad (1)$$

where ΔU is the output from the thermoelectric sensor and S is the thermoelectric sensitivity, i.e., the output electrical voltage generated by unit differential thermal power.

The differential thermal power can then be used to calculate the thermodynamic reaction parameters at 2914. In general, a biochemical reaction between a sample molecule M and a binding reagent X can be represented as:

$$n_1 X + n_2 M \rightarrow MX + \Delta H \quad (2)$$

where the reaction results in the product MX accompanied by a change of enthalpy ΔH. In ITC, the binding reagent X is titrated, i.e., successively added in known aliquots, into the sample, while the reaction heat is measured. The reaction heat is used to calculate the thermodynamic properties of the reaction, including the equilibrium binding constant $K_B = [MX]/[X][M]$ (where [·] denotes the equilibrium concentration of the species), stoichiometry $N = n_1/n_2$, and molar enthalpy change ΔH. In particular, the reaction heat can be calculated based on the differential thermal power. The biochemical reaction heat can be expressed as:

$$Q = \frac{NM_t \Delta H V_0}{2} \left[ 1 + \frac{r}{N} + \frac{1}{N K_B M_t} - \sqrt{\left(1 + \frac{r}{N} + \frac{1}{N K_B M_t}\right)^2 - \frac{4r}{N}} \right] \quad (3)$$

where Q is the biochemical reaction heat evolved at a molar ratio $r = X_t/M_t$, $V_0$ is the active volume for the reaction, $M_t$ is the total concentration of the sample, free plus bound, in the reaction cell of volume $V_0$, and $X_t$ is the total concentration of the reagent that is titrated into the sample solution.

In order to calculate the thermodynamic reaction parameters, an integral of the differential thermal power is computed. The resulting value is used as the biochemical reaction heat. A number of data points can be gathered based on the voltage measurements from a number of trials using different molar ratios. The resulting data can then be fitted to Equation (3) in order to calculate the thermodynamic reaction parameters. Fitting can be accomplished using fitting methods as known in the art for its intended purpose.

Figure 4A:
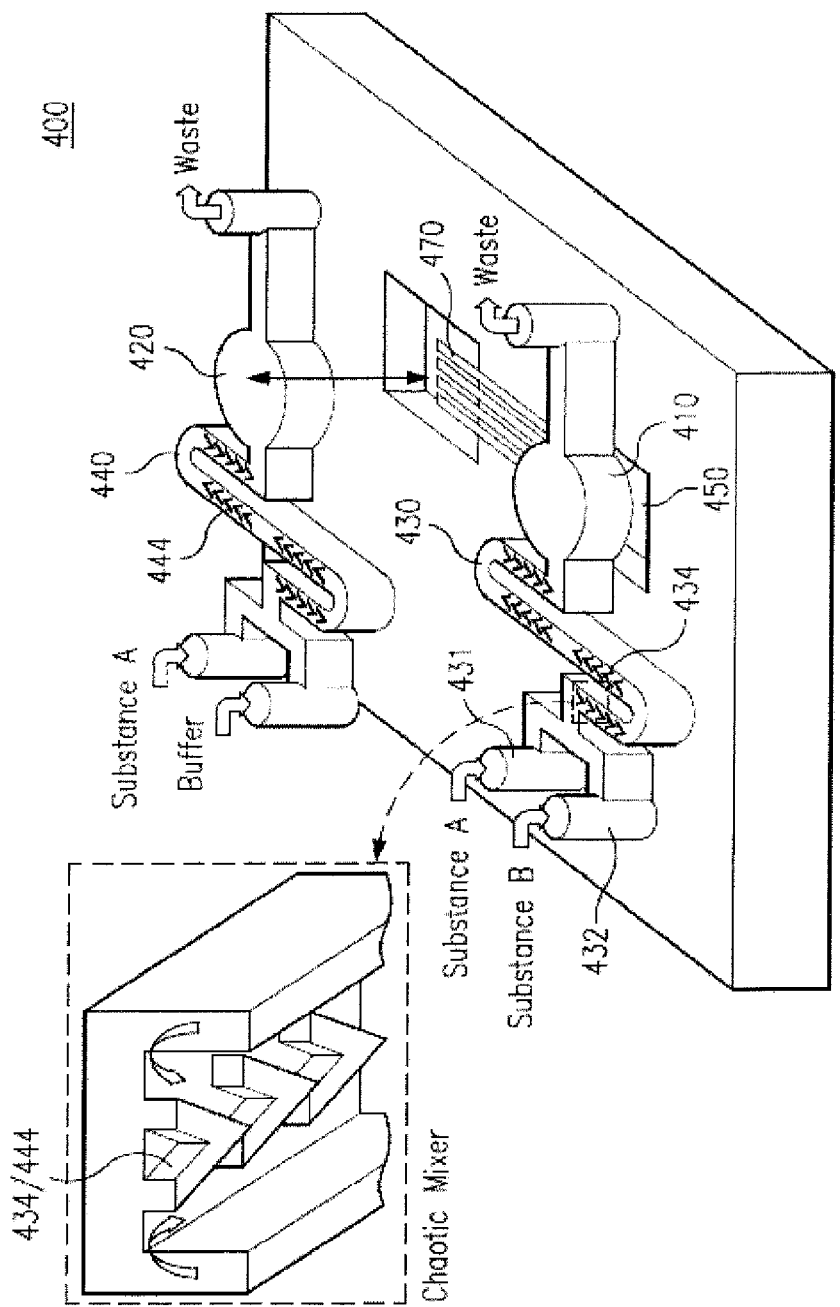
FIGS. 4a and 4b are schematics of a microdevice according to some embodiments of the disclosed subject matter for isothermal titration calorimetry.
Figure 4B:
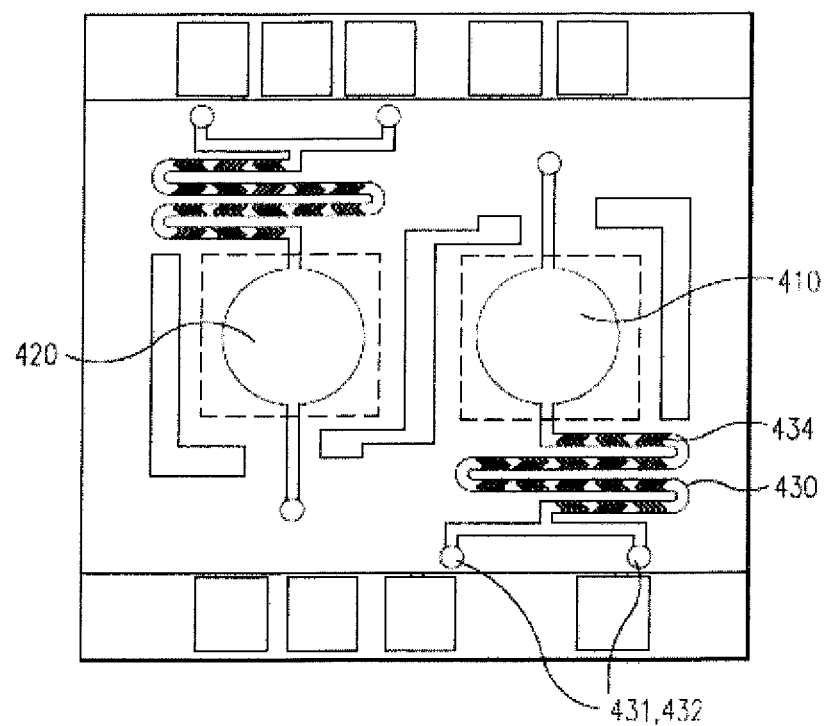

FIG. 4 is a schematic representation of the exploded view of a microdevice that is particularly suited for the ITC. The microdevice (400) includes a sample chamber (410) and a reference chamber (420), both situated on the thin film substrate (450) which includes a thermopile (470) for measuring the temperature differential of the sample chamber and the reference chamber during a heat scan. To facilitate mixing of the first and second substances (A and B), the microdevice further includes introduction channels (430, 440) for each of the sample and reference chambers (410, 420). Each of the introduction channels has two inlets (431, 432; 441, 442). Each of the introduction channels can be configured to provide passive chaotic mixing for a solution flowing through the channel. For example, as schematically shown in FIGS. 4a and 4b, the introduction channels (430, 440) can include a portion having a serpentine shape. Moreover, the introduction channels (430, 440) can includes internal ridges (434, 444) sufficient for creating turbulence in the solution flowing through channels. For example, as shown in the inlet of FIG. 4a, the introduction channels can include herringbone-shaped ridges in the ceiling.

The disclosed microdevice and methods of fabrication and use thereof are further illustrated in the examples below, which should not be considered as limiting the scope of the disclosed subject matter in any way.

Example 1

Fabrication of Microdevice

This example illustrates a procedure to fabricate the microdevice, which substantially follows the outlined procedure described above in connection with FIG. 2. In particular, a 6-μm thick polyimide film was spin-coated on a silicon wafer (precoated with silicon dioxide). The TMAH etching into the backside of the wafer in the areas that correspond to the calorimetric chambers created an approximately 50 μm-thick residual wafer layer. After the curing of the polyimide, a chromium/gold thin film (5/200 μm) was deposited by thermal evaporation onto the polyimide layer. A second layer of polyimide was then coated on the microheaters and temperature sensors. Subsequently, Sb and Bi thin films (0.5 and 1.2 μm) were thermally evaporated and patterned using a standard lift-off process to form a 50-junction thermopile using a standard lift-off process. A layer containing polyimide-PDMS mixture was further coated on the thermopile. The chamber housing structure was fabricated from PDMS using micromolding techniques on top of the thin film substrate, thereby forming the calorimetric chambers the calorimetric chambers each of cylindrical shape and 1 μL in volume (diameter: 2.5 mm and height: 200 μm), with a center-to-center separation of 4 mm. Xenon difluoride (XeF₂) gas-phase isotropic etching was used to remove the residual silicon layer on the wafer substrate from the backside of the thin film substrate. The integrated resistive microheaters each had a nominal resistance of 40 Ω and the temperature sensors each had a nominal resistance of 55Ω. Shown in FIG. 5 are the images of the PDMS housing structure and solid thermal substrate, as well as micrographs of the thermopile, integrated microheater and temperature sensor embedded in the thin film substrate.

Example 2

Calorimetric Measurement

In this example, the microdevice as fabricated according to Example 1 was calibrated and used to measure thermodynamic properties of certain biomolecules, e.g., thermodynamics of the unfolding of a protein.

A. Principle

DSC can measure differential heat capacity, i.e., the heat capacity difference between a sample and a reference material, as a function of temperature. When the sample and reference materials are subjected to identical temperature scanning, i.e., their temperatures are varied at a predetermined rate within a range of interest, the thermally induced activity of the sample molecules, which is either exothermic or endothermic, can cause a small temperature difference between the sample and reference materials (i.e., differential temperature or temperature differential). This differential temperature can be detected to reflect the differential power $$\Delta P = P_s - P_r \quad (4)$$

where $P_s$ and $P_r$ are the thermal power generated in the sample and reference materials, respectively. Therefore the differential heat capacity $$\Delta C_p = C_{ps} - C_{pr} \quad (5)$$

where $C_{ps}$ and $C_{pr}$ are, respectively, the heat capacities of the sample and reference materials, can be determined as:

$$\Delta C_p = \frac{\Delta P}{\dot{T}} = \frac{\Delta U}{S\dot{T}} \quad (6)$$

where $\dot{T}$ is the time rate of the controlled temperature of sample and reference materials, U is the output from the thermoelectric sensor that is employed to detect the differential temperature, and S is the device's sensitivity, i.e., the output electrical voltage generated by unit differential thermal power. Therefore, interpretation of the differential heat capacity can lead to determination of the fundamental thermodynamic properties of the sample material.

B. Device Calibration

Figure 6A:
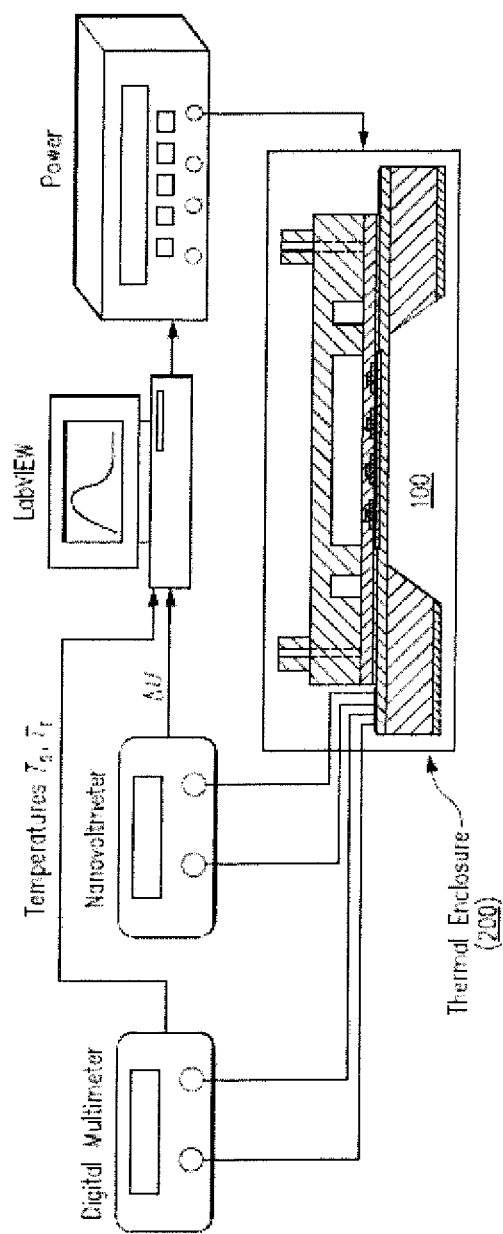
FIG. 6a is a schematic diagram of a testing setup for a calorimetric measurement using a microdevice according to some embodiments of the disclosed subject matter.

In order to measure the temperature differential between the two chambers, the thermopile need be first calibrated such that the voltage generated by the thermopile can be readily convert to temperature differential. As illustrated in FIG. 6a, to calibrate the MEMS DSC device, the on-chip microheaters were driven by a DC power supply (Agilent E3631A) and generated a constant differential heating power in the calorimetric chambers, while the temperature sensors were interrogated by a digital multimeter (Agilent 34410A) to monitor the temperatures of the calorimetric chambers. The thermopile output voltage, proportional to the differential temperature between the chambers, was measured by a nanovoltmeter (Agilent 34420A). The temperature control of the MEMS DSC device and thermoelectric measurements were automated using a personal computer via a LabVIEW-based program.

Figure 6B:
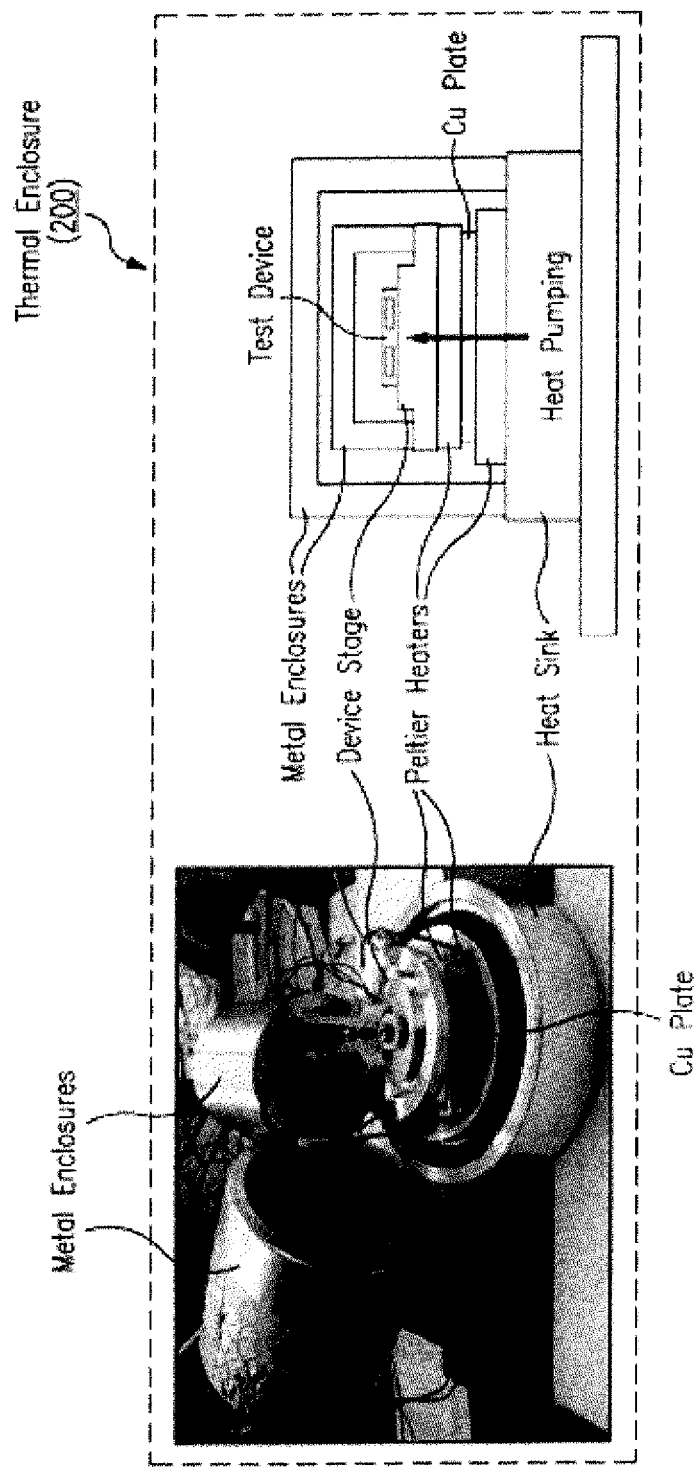
FIG. 6b shows the details of a custom-built, temperature-controlled thermal enclosure as compared with a schematic diagram of the thermal enclosure, according to some embodiments the disclosed subject matter.

A packaged MEMS DSC device (100) was housed in a custom-built, temperature-controlled thermal enclosure (200) consisting of multiple metal enclosures surrounding a metal stage on which the device was placed (FIG. 6b). This provided temperature scanning of the sample and reference solutions, as well as thermal isolation of the device package from the environment to minimize measurement noise. Multiple Peltier devices (Melcor UT15-12-40-F2) were located underneath the device stage, and by a power supply (Agilent E3631A), to add heat to or remove heat from the device. The temperature of the sample and reference chambers was controlled in closed loop by adjusting the voltage applied to the Peltier devices according to the feedback from the on-chip temperature sensors based on, for example, a proportional-integral-derivative (PID) algorithm.

During device calibration, the sample and reference chambers were both filled with 0.1 M Glycine-HCl buffer (pH 2.5), which was the buffer later used for protein unfolding measurements. A known, constant differential power was created by activating the microheater below the sample chamber while leaving the microheater underneath the reference chamber turned off. The temperature sensors were used to measure the temperatures of the thermopile's hot and cold junctions. The device output, i.e., the thermopile output voltage, was measured as a function of time to obtain the steady-state and transient responses to the differential heating power.

Figure 7:
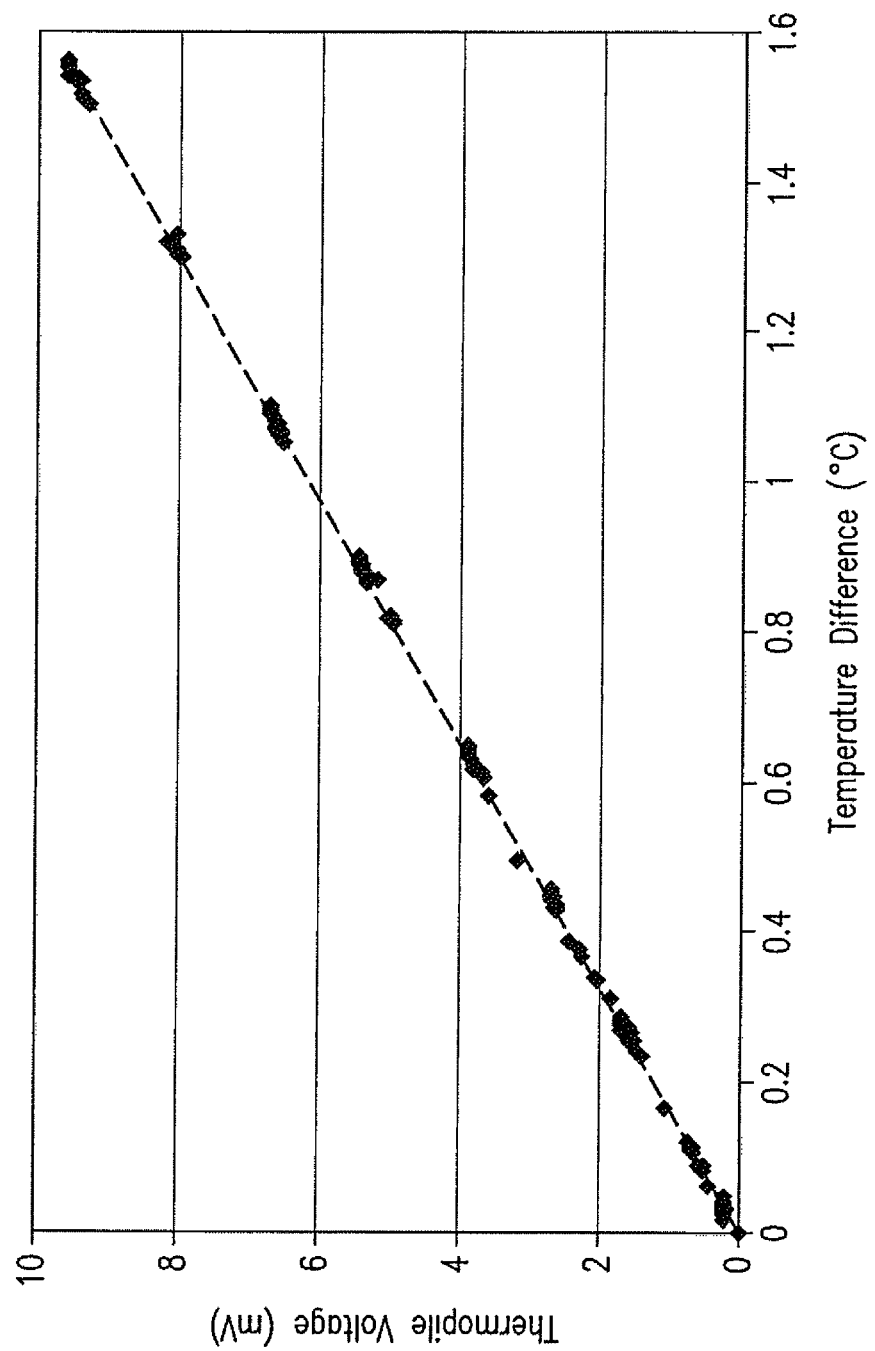
FIG. 7 is a plot showing the thermopile output voltage from a microdevice according to some embodiments the disclosed subject matter in response to constant temperature difference between the thermopile's hot and cold junctions.
Figure 8:
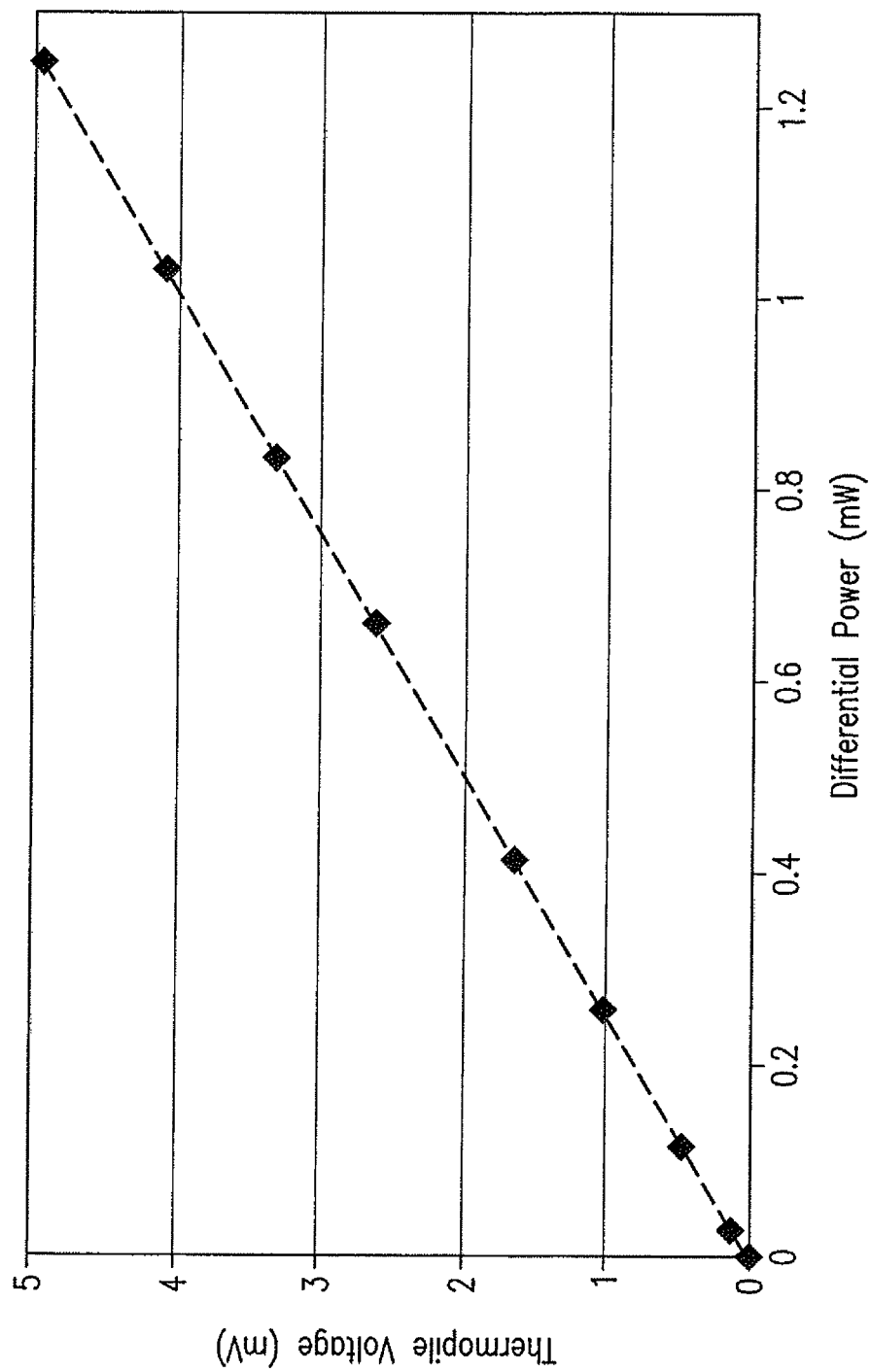
FIG. 8 is a plot showing a steady-state response (in terms of thermopile output voltage) from a microdevice according to some embodiments the disclosed subject matter in response to constant differential power between the two chambers of the microdevice.

The sensitivity of the thermopile integrated in the MEMS DSC device was calibrated at varying temperature difference between the hot and cold junctions, generated by on-chip heating (using the microheater underneath the sample chamber). The thermopile differential voltage exhibited a highly linear relationship with temperature difference (FIG. 7), showing a total thermoelectric sensitivity of 6.3 mV/° C. for the 50-junction thermopile. A Seebeck coefficient of 125 μV/K for each Sb—Bi thermocouple was obtained. In addition, the steady-state response of the MEMS DSC device was calibrated to varying differential power and observed again a highly linear relationship, yielding a nearly constant responsivity of S=4.0 mV/mW (FIG. 8). A root-mean-square (RMS) noise of approximately 40 nV in the device output was also observed, which was used to determine a baseline noise in the differential power. This corresponded to a detection limit of approximately 10 nW in differential thermal power measurement.

Figure 9:
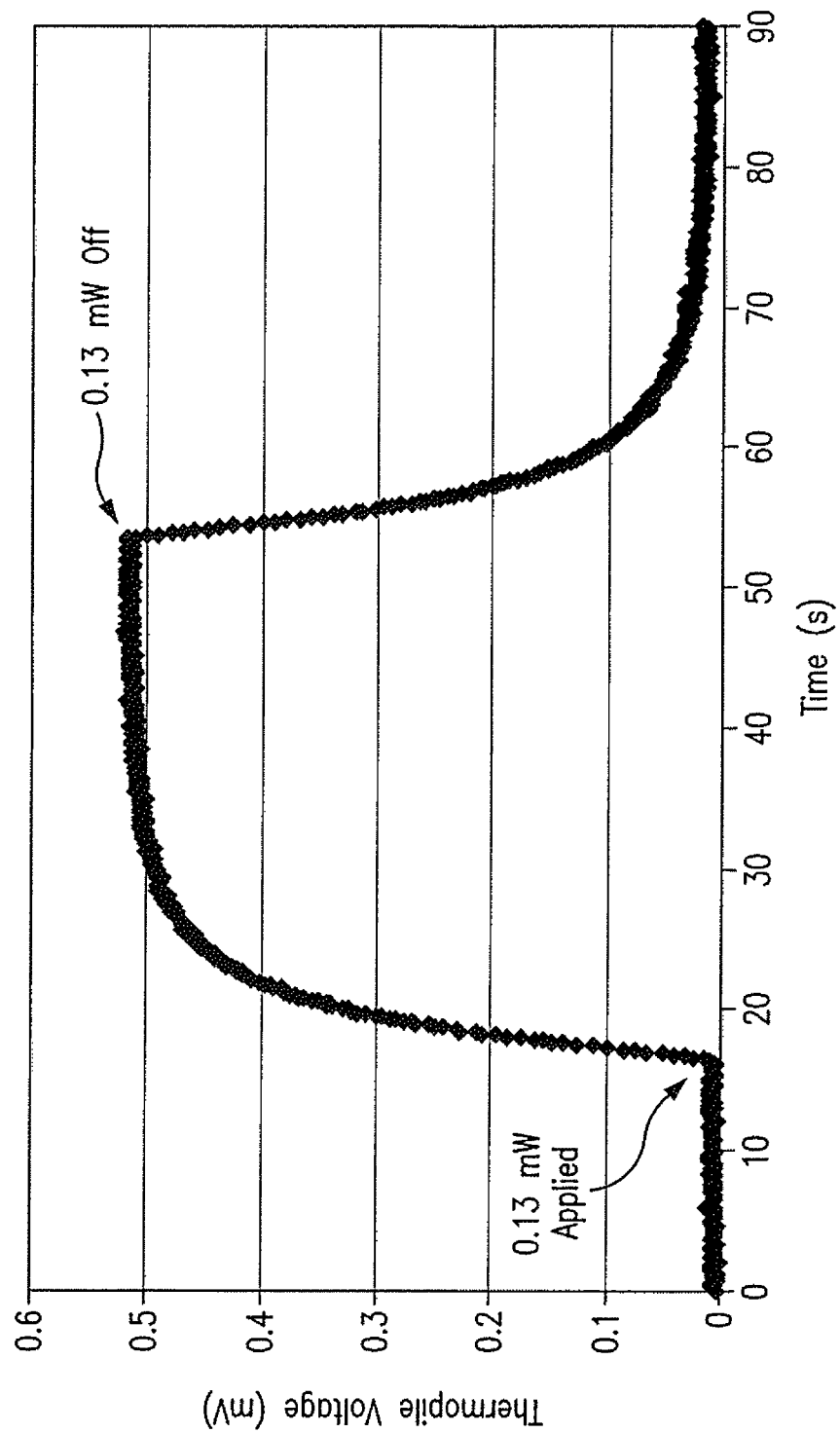
FIG. 9 is a plot showing the transient response of a microdevice according to some embodiments the disclosed subject matter with respect to a step differential power.

To characterize the transient response of the MEMS DSC device, a step differential power of 130 μW was initially applied to the calorimetric chambers and then turned off once the device output reached its equilibrium. The corresponding output voltage from the thermopile (FIG. 9) was found to exponentially grow with time upon the application of the differential power, while decay exponentially upon the removal of the differential power. The thermal time constant was approximately 2.0 s, calculated by fitting the experimental data to first-order exponential growth and decay functions.

C. Calorimetric Measurements

DSC measurements of biomolecules were performed using the calibrated microdevice, whose sample chamber and reference chamber were respectively filled with biological sample and buffer solutions, scanned in a range of temperature of interest. The temperature sensors were used to monitor the temperatures of calorimetric chambers while the device output was obtained in real time to compute the biomolecular thermal power. Before DSC measurements, the baseline in device output, i.e., the thermopile output voltage in the absence of a differential power input, during temperature scanning was measured with both calorimetric chambers filled with buffer solutions. Biological sample and buffer solutions were degassed with a vacuum chamber built in-house, metered with micropipettes, and introduced by a syringe pump (New Era Pump Systems, NE 1000).

The calibrated MEMS DSC device was employed to characterize protein unfolding, a common type of biomolecular conformational transition. For this purpose, the thermal enclosure provided temperature scanning of the MEMS DSC device at time rates as high as 6° C./min in the range of 10-90° C. with power consumption lower than 25 W. Using lysozyme prepared in 0.1 M Glycine-HCl buffer (pH 2.5) for purposes of demonstration, the device output was monitored while the sample and reference chambers, respectively filled with lysozyme and buffer, were scanned in a temperature range of 25-75° C. at a constant rate of 5° C./min.

Figure 10:
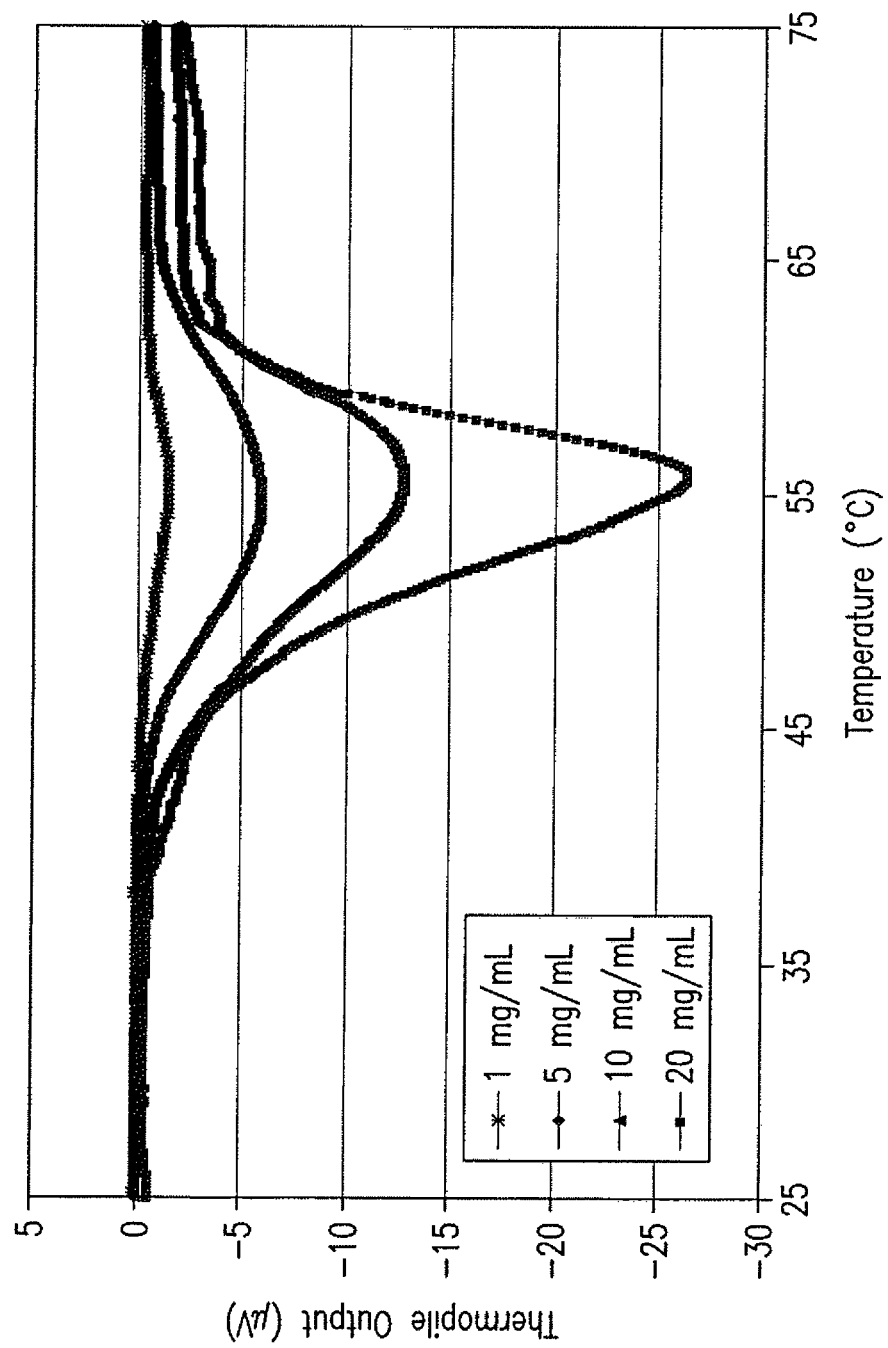
FIG. 10 is a plot showing the output of a microdevice according to some embodiments the disclosed subject matter as a function of temperature in a temperature scan during which the unfolding of lysozyme occurs.

The thermopile output voltage as a function of temperature, corrected by baseline subtraction, was measured at varying protein concentrations ranging from 1 to 20 mg/mL (FIG. 10). It was observed that the device output exhibited a concentration-dependent minimum within a certain temperature range, reflecting the endothermic nature of protein unfolding processes. Notably, the unfolding of lysozyme was detectable at 1 mg/mL, representing a significant improvement over the previously reported MEMS DSC device.

Figure 11:
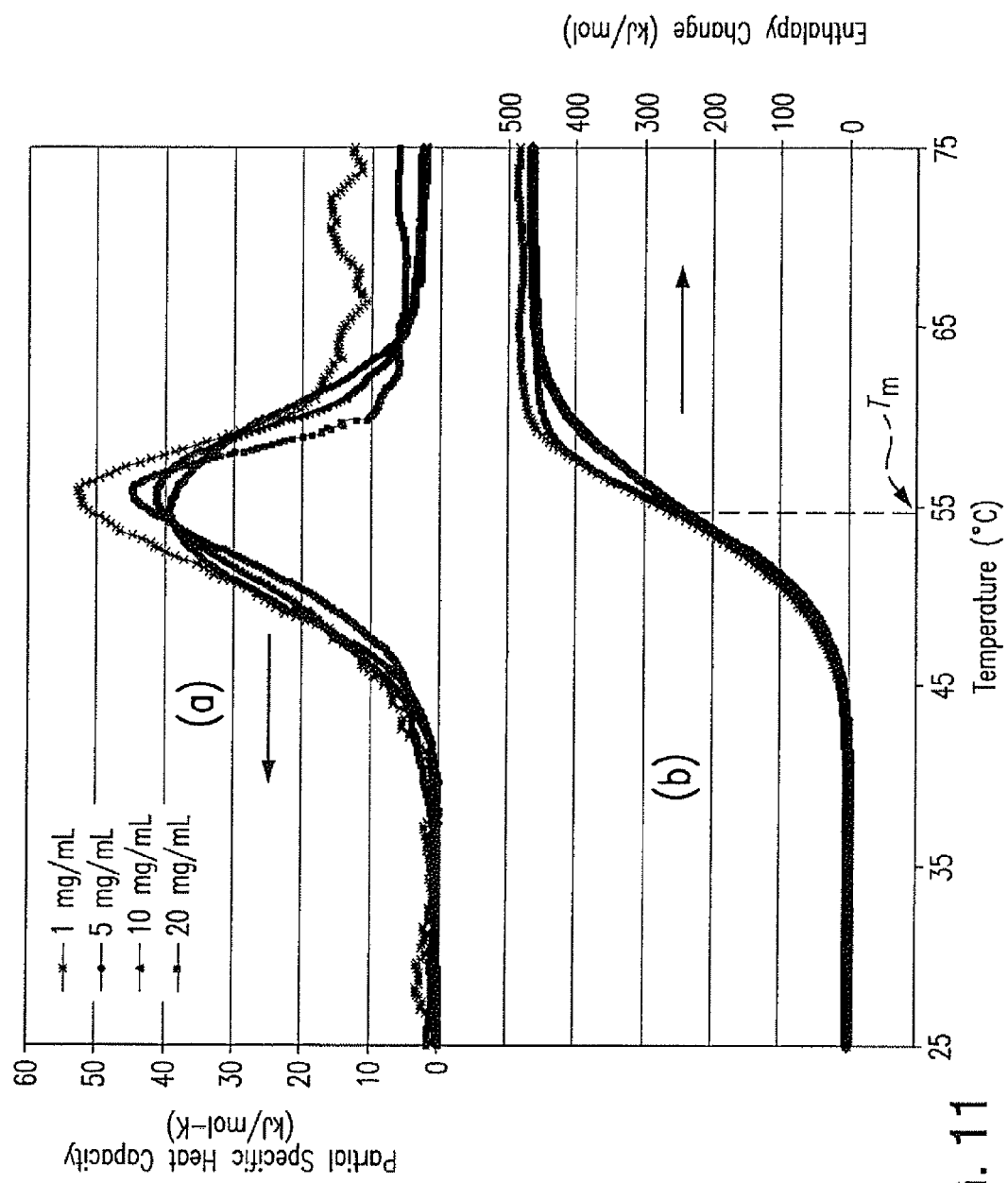
FIGS. 11a and 11b are plots showing partial specific heat capacity (11a) and change of molar enthalpy (11b) as a function of temperature during the unfolding of lysozyme, as measured by the microdevice according to some embodiments the disclosed subject matter.

Furthermore, the differential heat capacity between the chambers was computed from the differential voltage measurement (FIG. 10) using calibrated device sensitivity (4.0 mV/mW), allowing the thermodynamic properties of lysozyme to be obtained during its unfolding process, such as partial specific heat capacity (c) (FIG. 11a), the total change of molar enthalpy (i.e., enthalpy per mole of lysozyme) ($\Delta H$), and melting temperature ($T_m$, defined as the temperature at which the change of molar enthalpy achieves 50% of $\Delta H$) (FIG. 11b). Despite the amplitude difference of device output at various protein concentrations, they all yielded consistent estimates of the thermodynamic properties associated with the protein unfolding process. In particular, the profile shape of c was generally not influenced by protein concentration, and $\Delta H$ was consistently determined to be approximately 450 kJ/mol with a corresponding melting temperature $T_m$ of approximately 55° C. These results agree well with published data, which are typically in the range $\Delta H$=377-439 kJ/mol and $T_m$=55-58.9° C. for lysozyme, demonstrating the potential utility of the MEMS DSC device disclosed herein for biomolecular characterization with significantly reduced sample consumption at practically relevant protein concentrations.

The effects of the temperature scanning rate on DSC measurements were also investigated. Using 20 mg/mL lysozyme prepared in 0.1 M Glycine-HCl buffer (pH 2.5) for example, the unfolding of lysozyme at temperature scanning rates were varied from 1-6° C./min. The thermopile output voltage (again corrected by baseline subtraction) (FIG. 12a) exhibited a consistent dip in the same temperature range for protein unfolding as indicated above, with an amplitude increasing with the temperature scanning rate. This is consistent with a larger heat flux resulting in a higher endothermic power through phase transformations.

Figure 12:
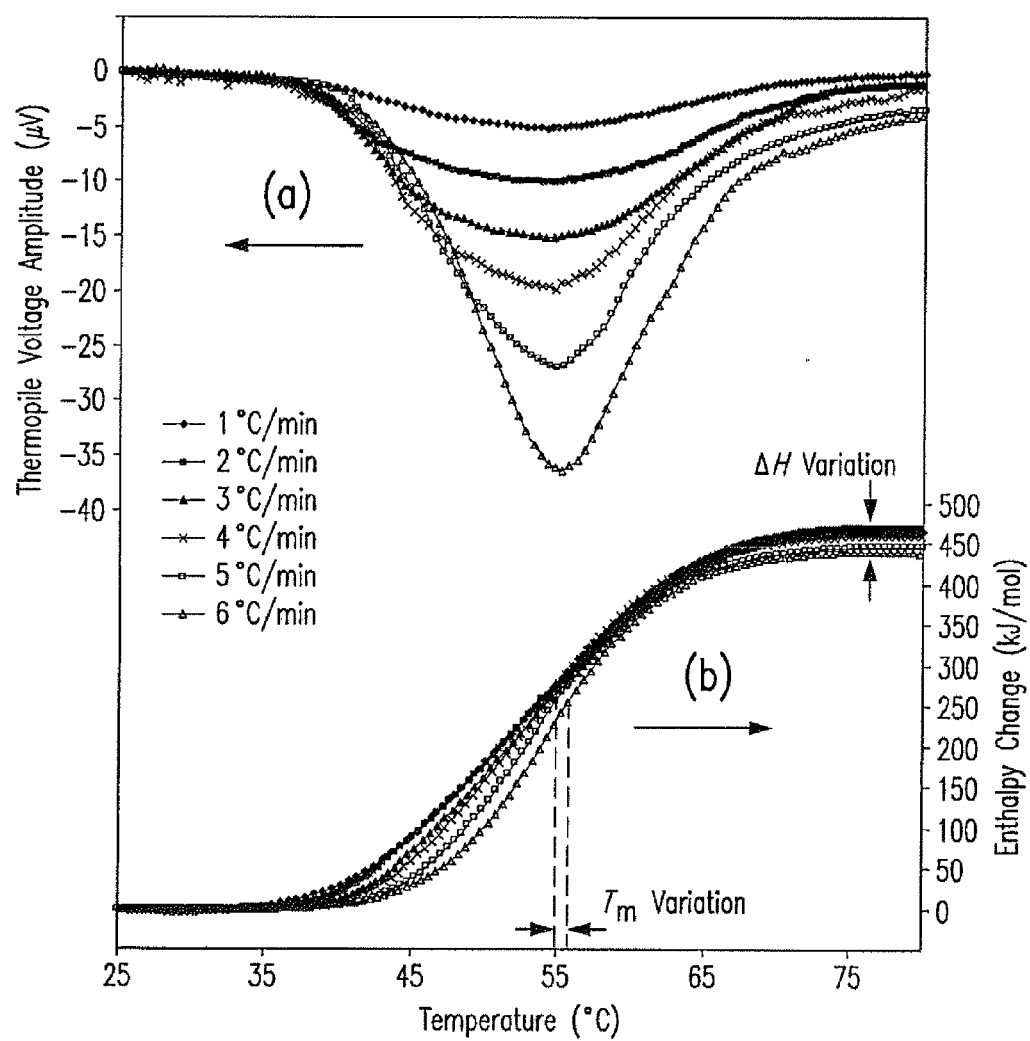
FIGS. 12a and 12b are plots showing the output of a microdevice according to some embodiments the disclosed subject matter (10a) and change of molar enthalpy as a function of temperature during the unfolding of lysozyme at varying temperature scanning rates.

These data were then used to compute the change of molar enthalpy (FIG. 12b). Although a slight shift in the device output could be observed (FIG. 12a) as temperature scanning rate increased, the thermodynamic properties associated with the protein unfolding process were found generally consistent, with a standard variation in $\Delta H$ of approximately 50 kJ/mol (i.e., ±5% of the mean value of $\Delta H$) and a standard variation in $T_m$ of less than 1° C. (FIG. 12b). Notably, for temperature scanning at 1-5° C./min, the $T_m$ values were almost the same. This demonstrates the measurement consistency using the MEMS DSC device of the disclosed subject matter, and indicates that a temperature scanning rate as high as 5° C./min is adequate for the measurement of lysozyme unfolding.

Example 3

AC-DSC Measurement

This Example illustrates the method of carrying out a AC-DSC measurement, as described above based on a microdevice presently disclosed. This MEMS AC-DSC approach can potentially enable measurements of low-abundance biomolecules with improved accuracy, as demonstrated by the application of the device to AC-DSC measurements of the unfolding of lysozyme.

A. Principle

AC-DSC can monitor the differential heat capacity, i.e., the heat capacity difference between a sample and a reference material, by varying the materials' temperatures at a specified constant rate via a thermally isolated enclosure equipped with temperature control functionalities, superimposed with a temporally periodic variation via identical AC modulation heating applied to the sample and reference (FIG. 3). The differential heat capacity can be obtained by the measurement of the differential temperature, i.e., the temperature difference between the sample and reference materials.

B. Fabrication of the Microdevice, System Setup and Calibration

The AC-DSC measurement was carried out using a microdevice schematically depicted in FIG. 1 and fabricated according to the procedure described in Example 1. While other device parameters, including the dimension and volume of the chambers, thickness of polyimide paraphragms, and characteristics of the microheaters and temperature sensors, are largely the same as those of the microdevice described in Example 1, the Sb—Bi thermopile used in this Example includes 100 junctions rather than 50 junctions in Example 1.

Figure 13:
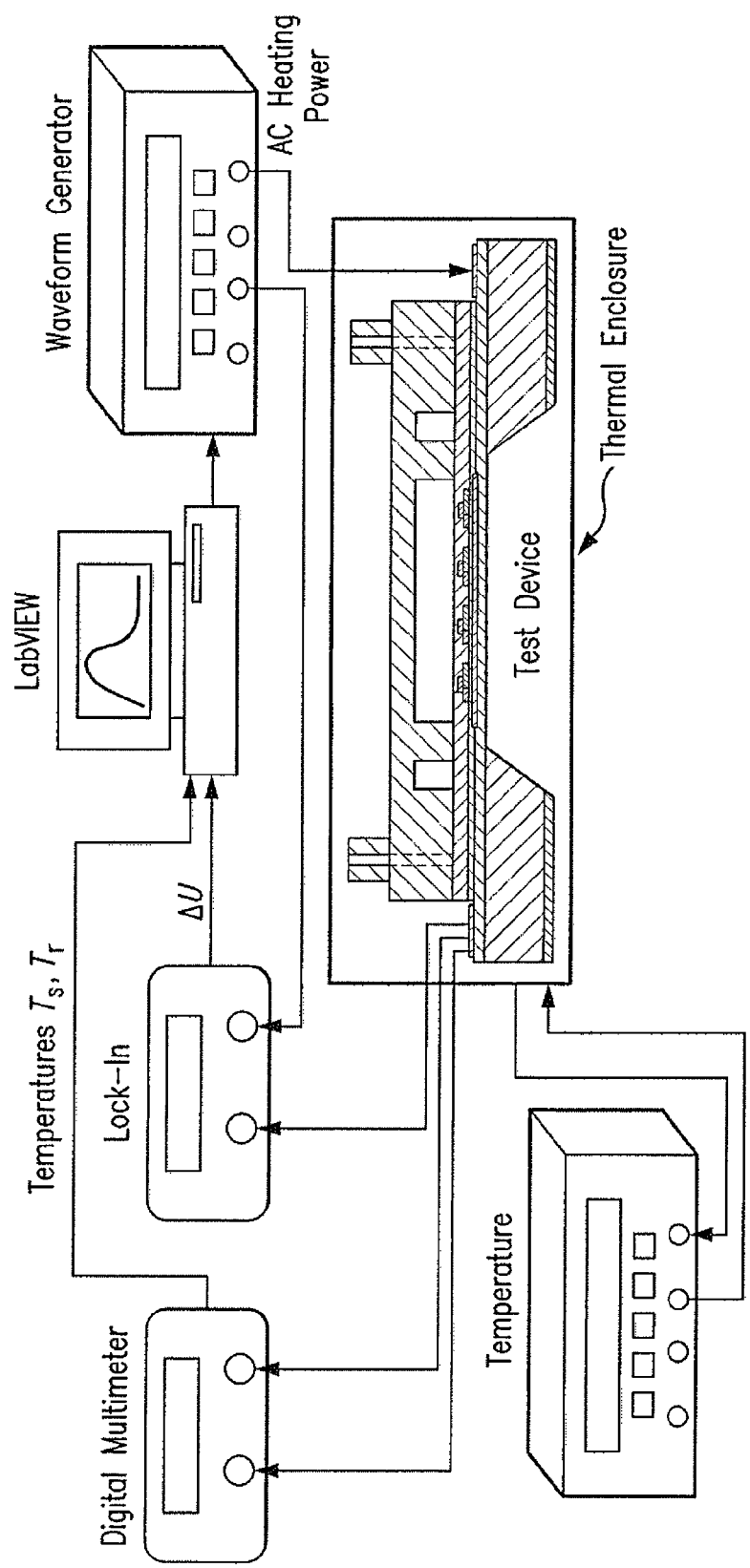
FIG. 13 is a schematic diagram showing an experiment setup for AC-DSC measurements according to some embodiments of the disclosed subject matter.

The DSC measurement system was configured similarly to that of Example 2. The microdevice was also placed in a thermal enclosure built in-house. The temperature of the sample stage in the thermal enclosure was controlled in closed-loop via a proportional-integral-derivative (PID) algorithm implemented by a commercial temperature controller (Lakeshore 331). The on-chip microheaters driven by a DC power supply (Agilent E3631A) were used to generate a constant differential power input, while for modulated heating, a square-wave AC voltage generated by a waveform generator (Agilent 33220A) was applied (FIG. 13). The temperature sensors were used to detect the real-time temperature inside each of the calorimetric chambers by a digital multimeter (Agilent 34410A). During device calibration, the thermopile output voltage was measured by a nanovoltmeter (Agilent 34420A), while during AC-DSC measurement, the amplitude and phase of thermopile voltage were measured by a lock-in amplifier (Stanford Research Systems SR830) referenced by the same AC modulation square wave from the waveform generator. The AC-DSC measurement was fully automated through a LabVIEW program.

The methods for calibrating the DC performance of the MEMS device were substantially the same as described in Example 2. The baseline in device output, i.e., the thermopile voltage with no differential power input during temperature scanning, was measured with both chambers filled with buffer solutions. During calibration of the device's modulation frequency dependence and AC-DSC measurements, the sample chamber was filled with a biological sample solution while the reference chamber was filled with the buffer solution. Biological sample and buffer solutions were degassed with a vacuum pump built in-house and then introduced into the device's calorimetric chambers with micropipettes.

Figure 14:
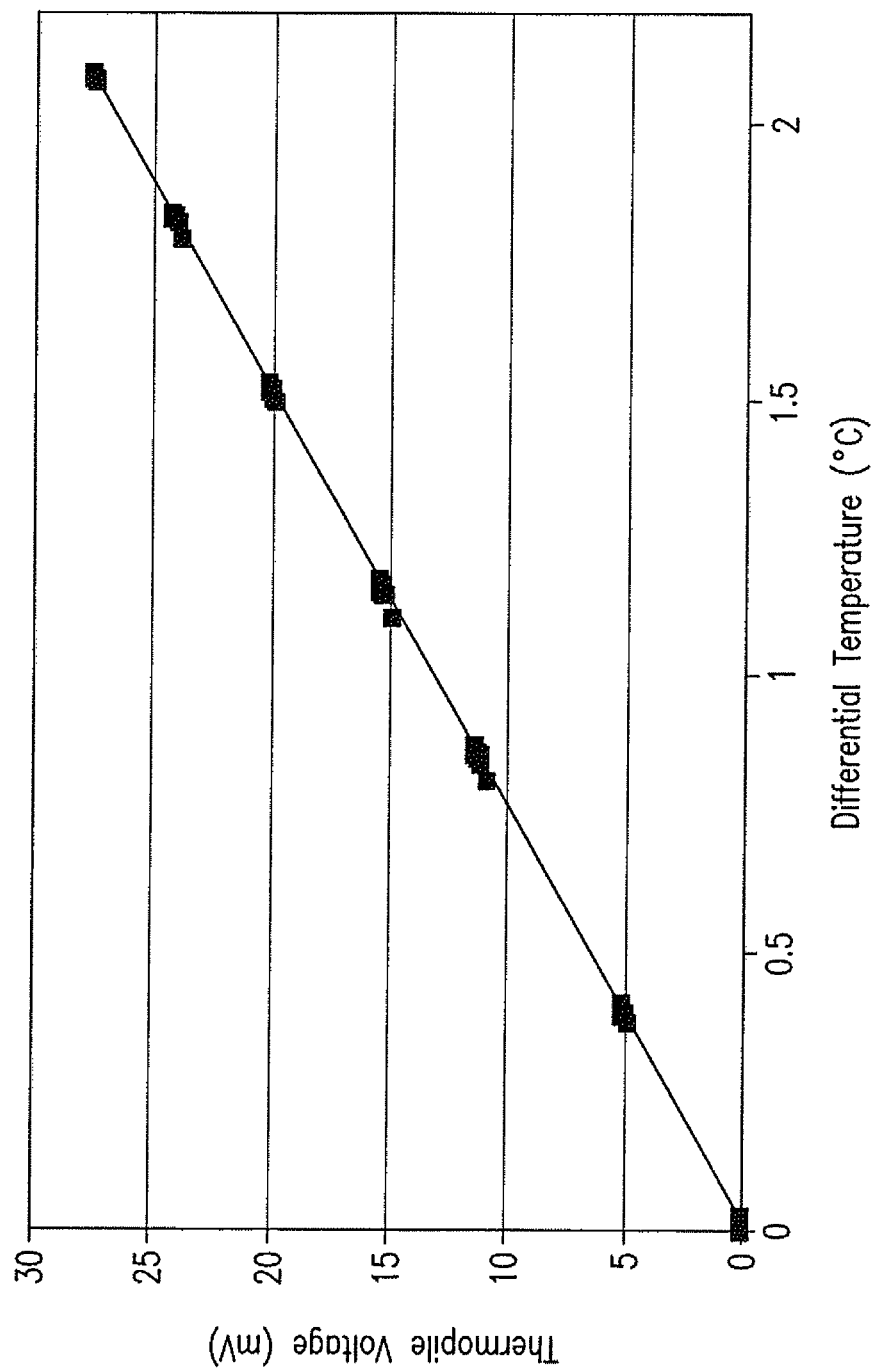
FIG. 14 is a plot showing the output voltage of the thermopile of a microdevice according to some embodiments of the disclosed subject matter in response to constant differential temperature between its hot and cold junctions.
Figure 15:
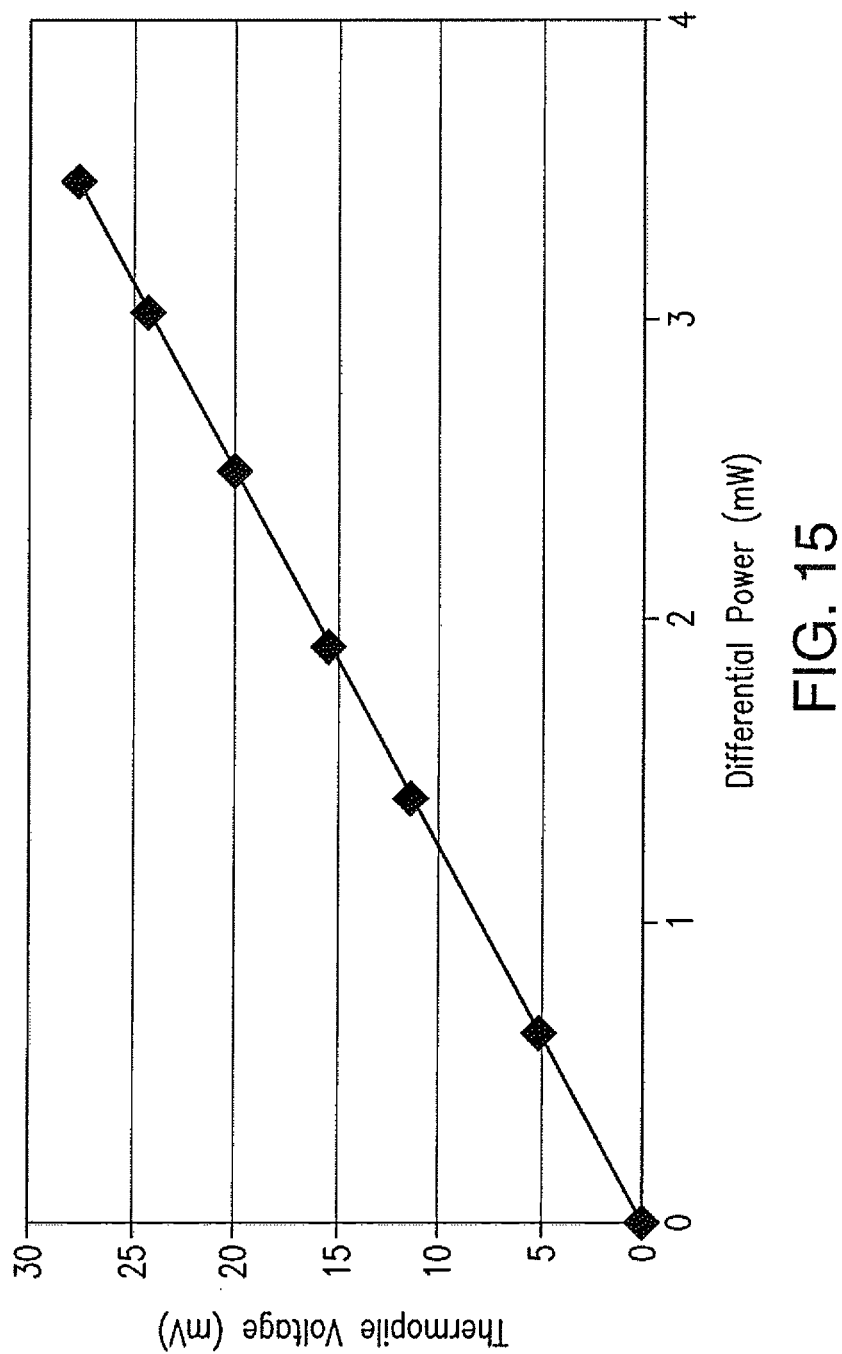
FIG. 15 is a plot showing a steady-state response (in terms of thermopile output voltage) from a microdevice according to some embodiments the disclosed subject matter in response to constant differential power between the two chambers of the microdevice.
Figure 16:
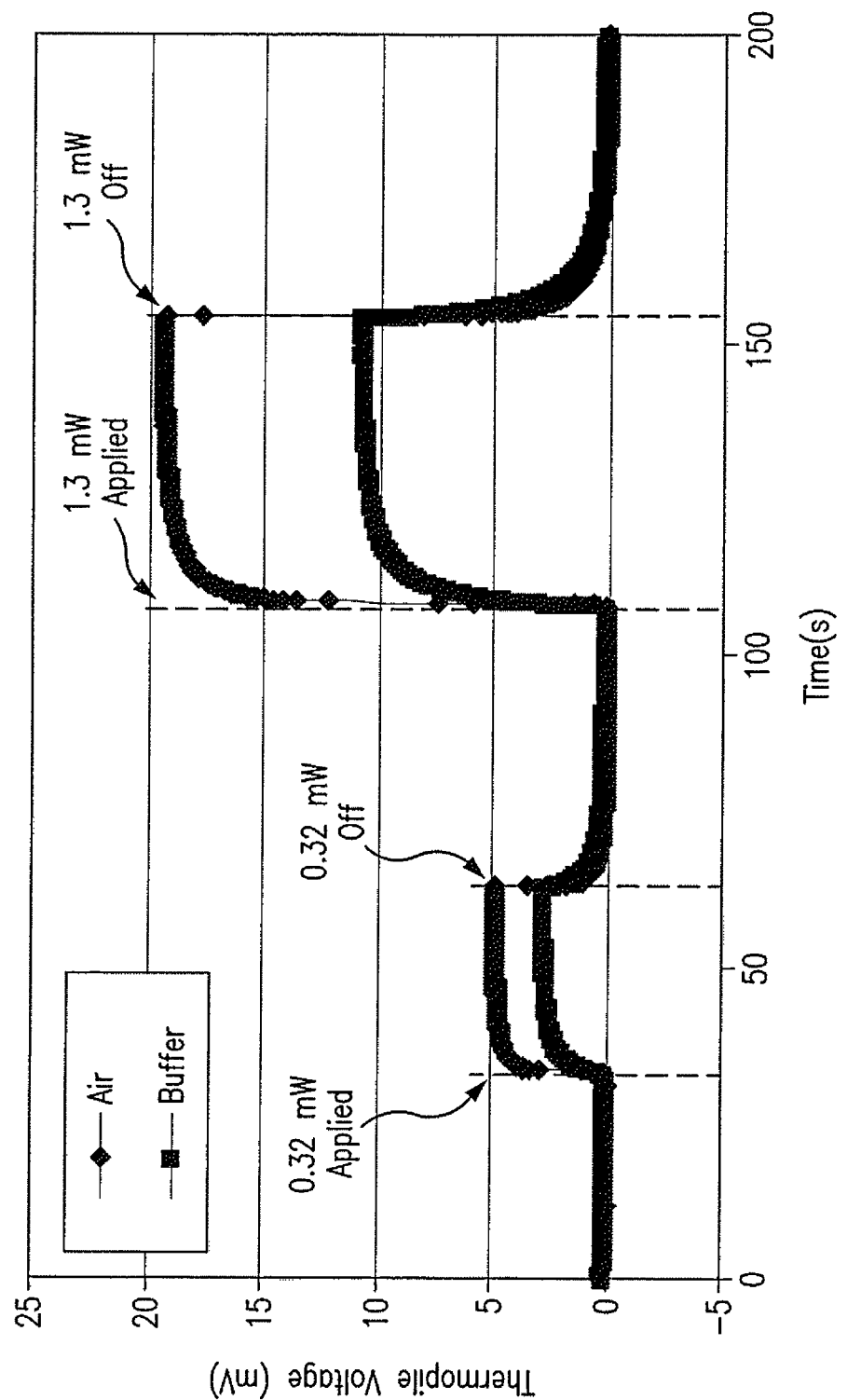
FIG. 16 is a plot showing the transient response of a microdevice according to some embodiments the disclosed subject matter with respect to a step differential power.

The thermopile in the MEMS device was first calibrated, and the results showed that 100-junction thermopile had a sensitivity of 13.0 mV/° C. (FIG. 14), corresponding to a Seebeck coefficient of (per Sb—Bi thermoelectric junction) of approximately 130 µV/° C. The steady-state response of the device to a constant differential power was then measured, and exhibited a highly linear relationship with a DC responsivity of 8.0 mV/mW (FIG. 15). These results were consistent with calibration results from the 50-junction Sb—Bi thermopile in Example 2. Additionally, the transient response of the device was determined. The calorimetric chambers, both of which were filled either with air or with 0.1 M Glycine-HCl buffer (pH 2.5), were subjected to a step differential power (0.32 or 1.30 mW). Results from these measurements are shown in FIG. 16. The dependence of the thermopile voltage on time can be represented by a first order exponential increase. The thermal time constant thus obtained was 0.8 s when the chambers were filled with air, and 2.0 s when they were filled with buffer solution. These values were independent of the applied differential power, and were smaller than conventional AC calorimetric measurements.

Figure 17:
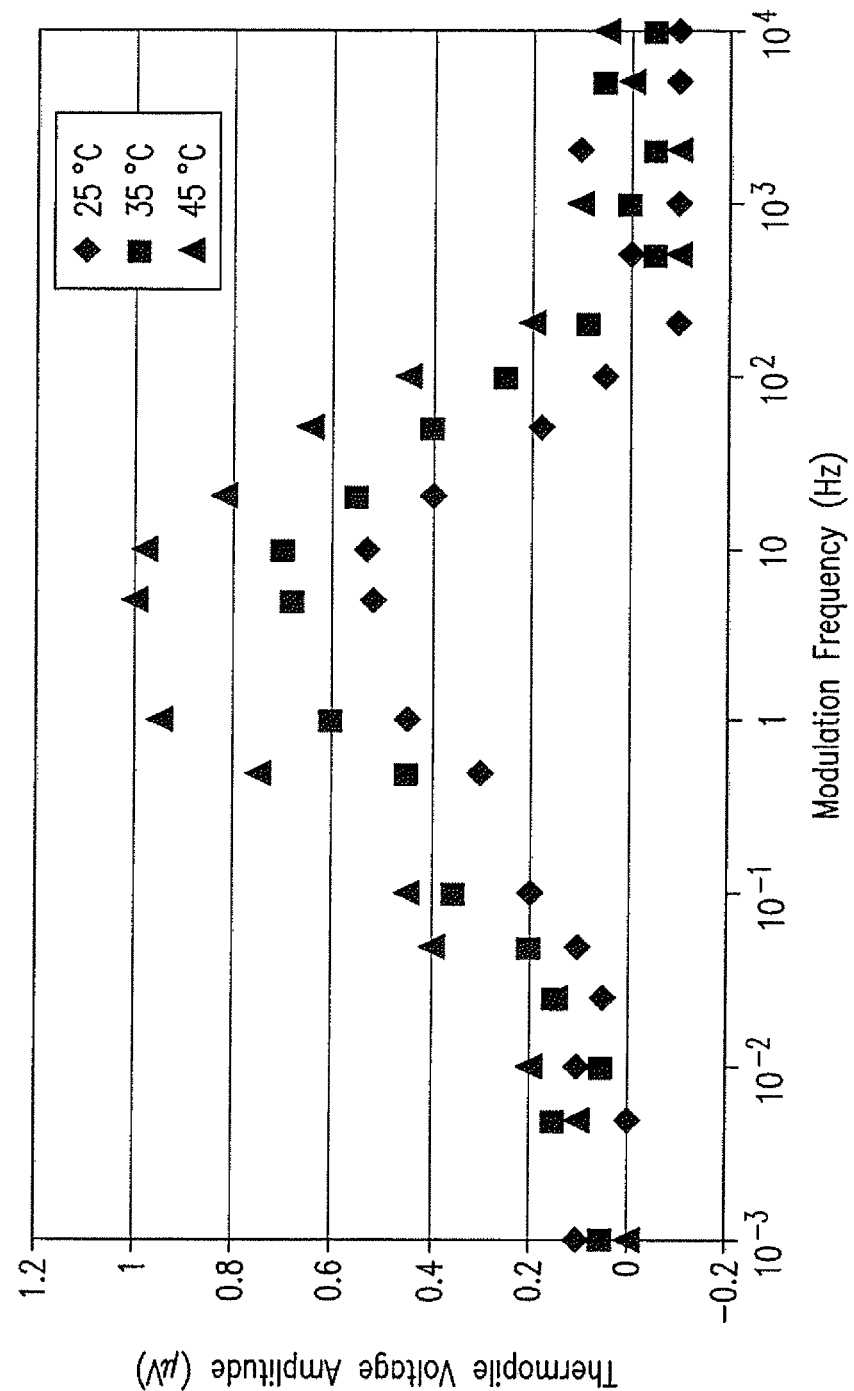
FIG. 17 is a plot showing the frequency dependence of thermopile voltage (baseline subtracted) of a microdevice according to some embodiments the disclosed subject matter, where the sample chamber was filled with lysozyme (20 mg/mL) and the reference chamber was filled with 0.1 M Glycine-HCl buffer (pH 2.5).

Further, the modulation frequency dependence of the device response to the applied differential power was investigated. To better simulate the application for AC-DSC measurement of protein unfolding process, the sample chamber was filled with lysozyme (20 mg/mL, prepared in 0.1 M Glycine-HCl, pH 2.5) as a sample, while the reference chamber was filled with Glycine-HCl buffer. The chambers were maintained at a constant temperature (25, 35, or 45° C.), and subjected to AC heating (voltage amplitude: 1 V). The dependence of the thermopile voltage amplitude on the modulation frequency, corrected by baseline subtraction, is shown in FIG. 17. It can be seen that the thermopile voltage increased with temperature at almost all modulation frequencies, which can be explained by the temperature-dependence of the protein's heat capacity. Also, the device output (and hence sensitivity) appear greatest in a modulation frequency range of 0.5 to 20 Hz (FIG. 17), suggesting a reduced heat loss to the ambient by choice of modulation frequency. Therefore, modulation frequencies in this range were used below in calorimetric measurements of protein unfolding processes, as further described below.

C. AC-DSC Measurements

The MEMS AC-DSC device calibrated above was used to measure the thermal behavior of protein unfolding. Using lysozyme at different concentrations (10 and 20 mg/mL, prepared in 0.1 M Glycine-HCl buffer, pH 2.5) for example, the temperature of the calorimetric chambers was varied from 25 to 82° C. at a rate of 5° C./min in combination with AC modulation via a heating voltage amplitude of 3.5 V at a constant frequency (1, 5, or 10 Hz). The periodic temperature variation resulting from the AC modulation heating had an amplitude of approximately 0.2° C.

Figure 18:
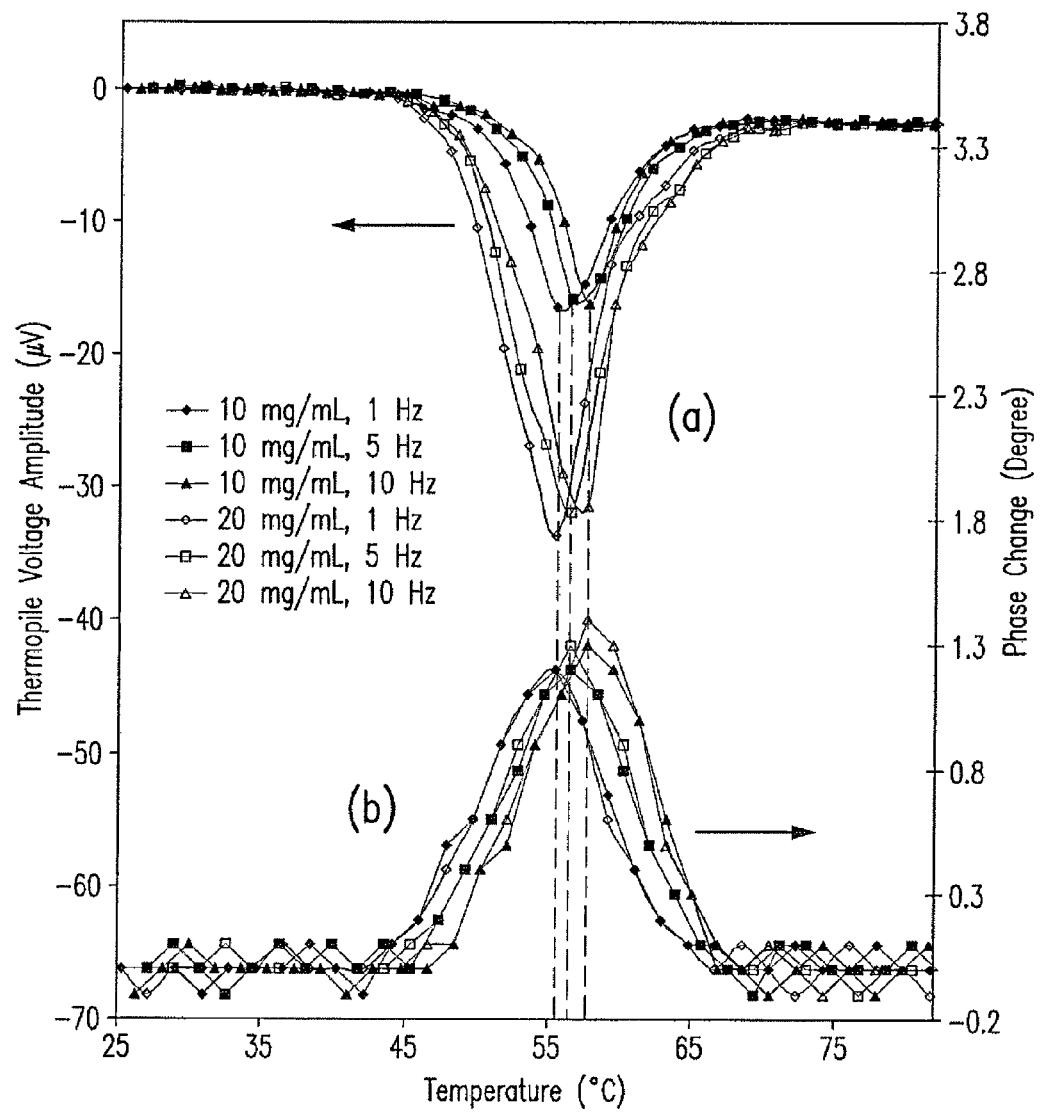
FIGS. 18a and 18b are plots showing changes in (18a) amplitude, and (18b) phase, of the thermopile voltage as a function of temperature during the unfolding of lysozyme at different lysozyme concentrations and AC modulating frequencies, as measured on a microdevice according to some embodiments the disclosed subject matter.

The measured thermopile voltage amplitude (FIG. 18a), again corrected by baseline subtraction, showed a concentration-dependent dip during the unfolding process, consistent with the endothermic nature of protein unfolding. In addition, despite differences in thermopile voltage amplitude for different lysozyme concentrations, the phase of the thermopile voltage (FIG. 18b) had identical changes throughout the unfolding process, which remained unchanged in the native and unfolded states when a two-state protein denaturation model was adopted. Furthermore, both the amplitude and phase changes of the thermopile voltage exhibited clear shifts with the modulation frequency, which could be attributed to the unsynchronized thermal response of the device to AC heating. However, at a fixed protein concentration, the profiles of the thermopile voltage amplitude and phase changes had virtually the same shape at different modulation frequencies, showing the suitability of the frequency choice for the MEMS-based AC-DSC measurements.

Figure 19:
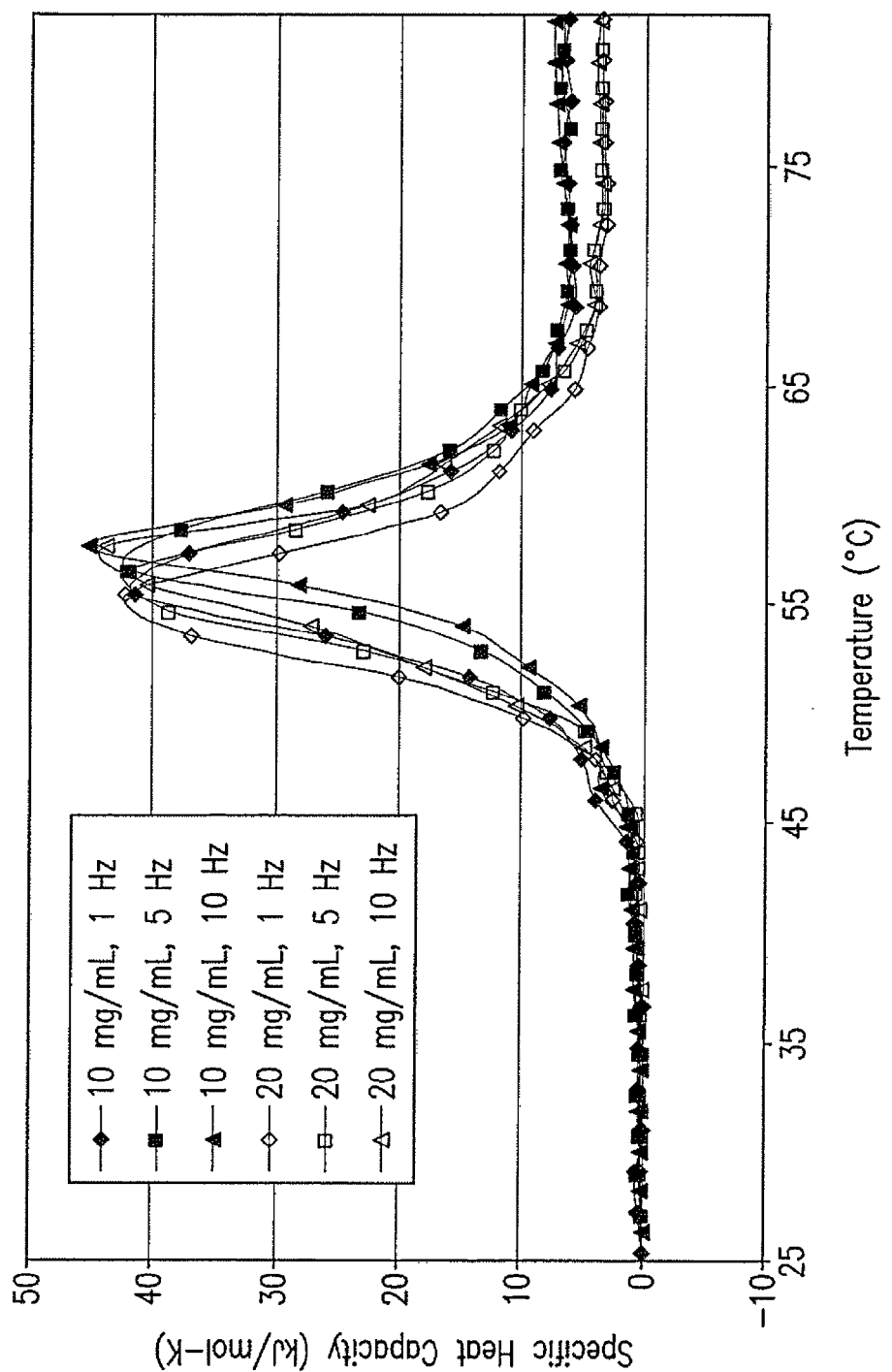
FIG. 19 is a plot showing specific heat capacity of lysozyme as a function of temperature during the unfolding of lysozyme at different lysozyme concentrations and AC modulation frequencies, as measured on a microdevice according to some embodiments the disclosed subject matter.
Figure 20:
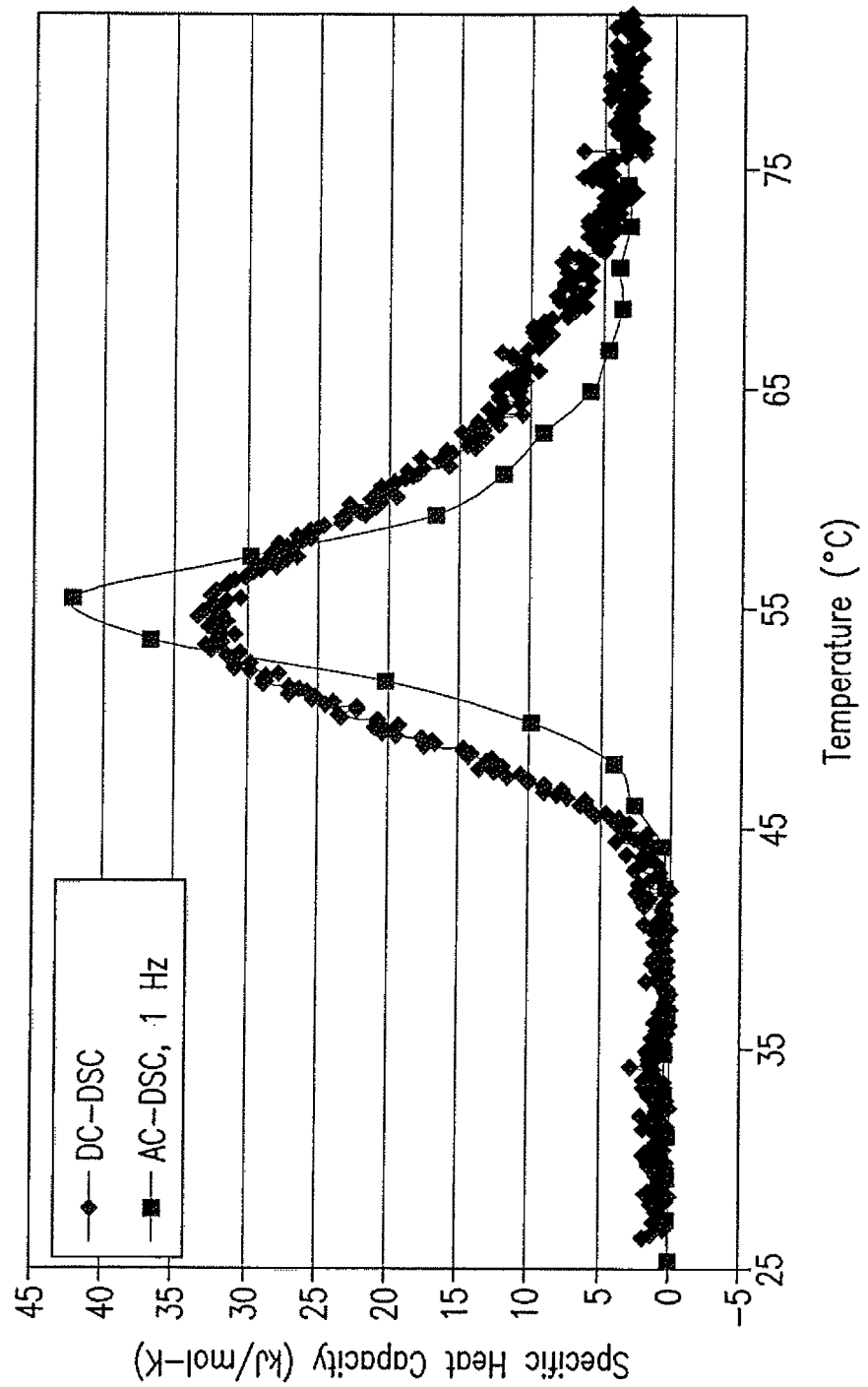
FIG. 20 is a plot showing a comparison between a DC-DSC measurement and an AC-DSC measurement for specific heat capacity of lysozyme during its unfolding process, using a microdevice according to some embodiments the disclosed subject matter.

The apparent melting temperature ($T_m$) of lysozyme during an unfolding process, i.e., the temperature at which the phase change of device output reaches its peak, was found to be in the range of 55-58° C. (FIG. 18), depending on the modulation frequency. Meanwhile, the specific heat capacity (c) of the protein as a function of temperature can be computed from the thermopile voltage amplitude (FIG. 19). It be seen that although there again existed a slight shift in c throughout the unfolding process induced by modulation frequency, the profile shape of c was not influenced by the modulation frequency. Moreover, at each modulation frequency, the calculated value of c does not differ significantly at different protein concentrations (FIG. 19), showing that the AC-DSC measurements were accurate. There was also a difference in the specific heat capacity ($\Delta c$) between the protein's native and unfolded states, which was calculated consistently to be 3.0 kJ/mol·K regardless of the modulation frequency. These results are consistent with established results from DC-DSC characterization. Compared with DC-DSC measurements in the same MEMS device without using temperature modulation (FIG. 20), AC-DSC can offer much reduced noise levels and improved measurement accuracies, and therefore holds the potential to enable characterization of biomolecular interactions at low concentrations Example 4

MEMS-Based Isothermal Titration Calorimetry

This Example illustrates the method of performing isothermal titration calorimetric measurement, as described above based on a microdevice disclosed herein.

A. Principle

Consider a solution-phase biochemical reaction $n_1 A + n_2 B \leftrightarrows C + \Delta H$, where A and B are reactants (e.g., a ligand and a sample, respectively) and C is a product. The reaction is accompanied by a change of enthalpy $\Delta H$. In ITC, the ligand can be titrated, or successively added in known aliquots, into the sample, while the reaction heat is measured. This data can then used to determine the thermodynamic properties of the reaction, including the equilibrium binding constant $K_B=[C]/[A][B]$ (the square brackets denote the equilibrium concentration of the species), stoichiometry $N=n_1/n_2$, and enthalpy change ($\Delta H$).

B. Device Setup and Calibration

Figure 21A:
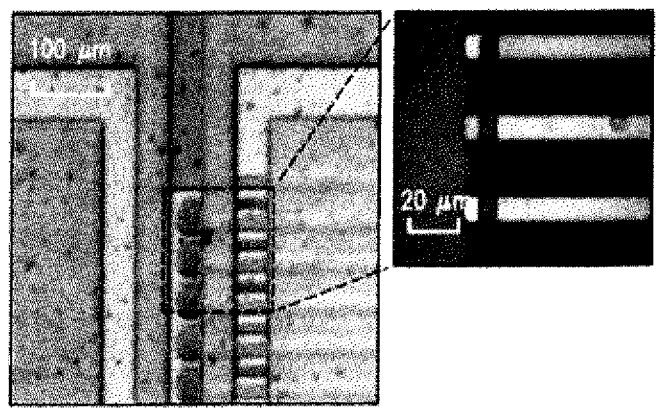
FIG. 21 are images of certain elements of a microdevice for isothermal titration calorimetry according to some embodiments of the disclosed subject matter.
Figure 21B:
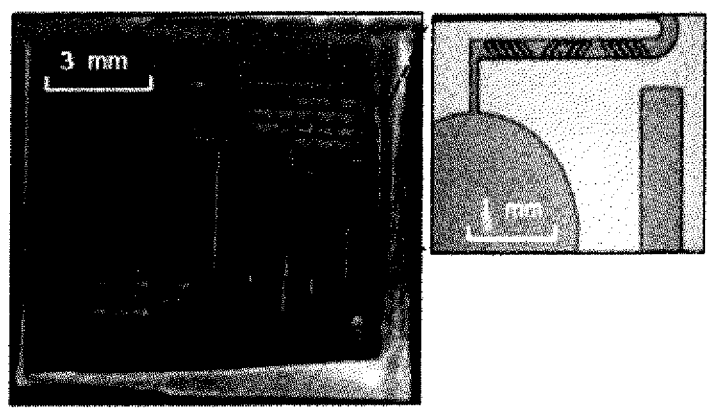
Figure 22:
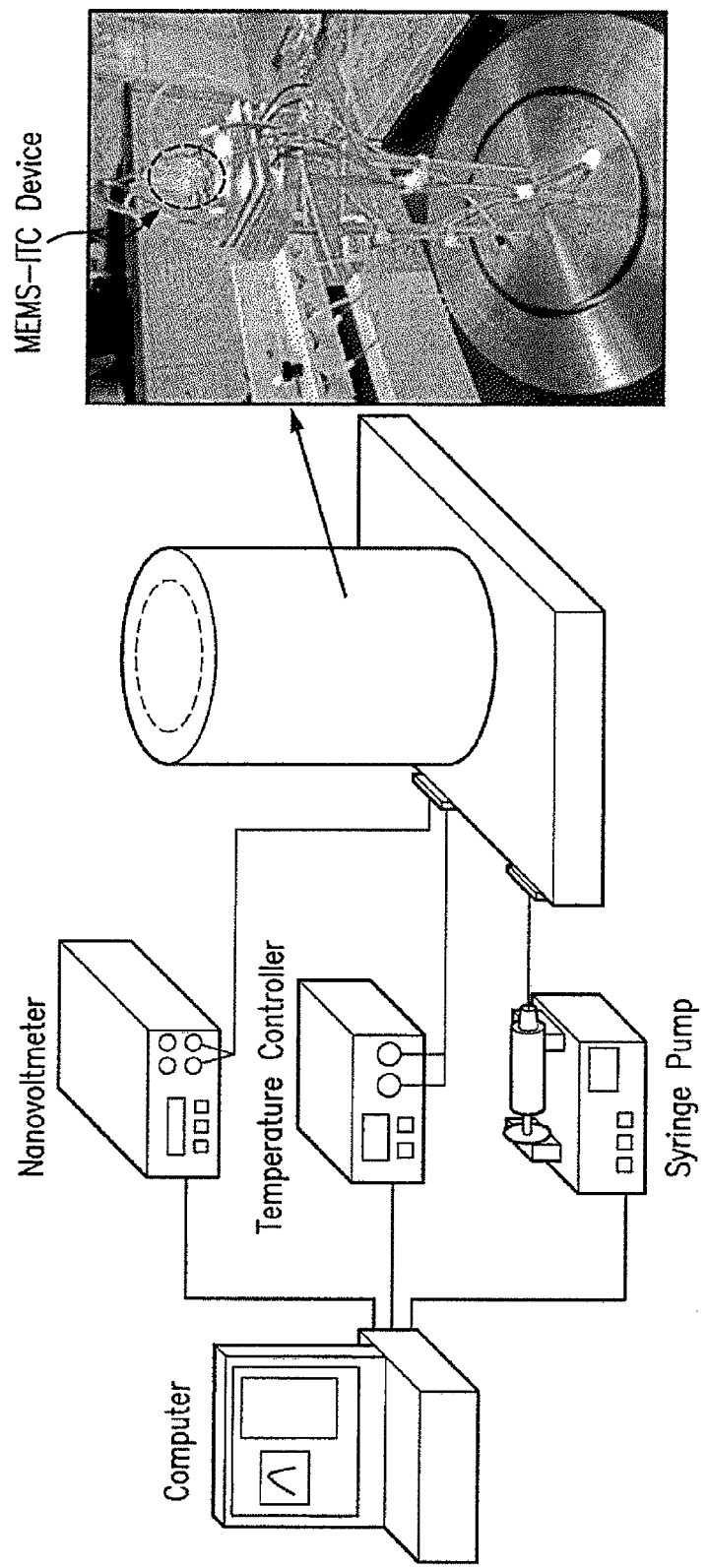
FIG. 22 is a schematic diagram showing the experimental setup for isothermal titration calorimetry according to some embodiments of the disclosed subject matter.
Figure 23A:
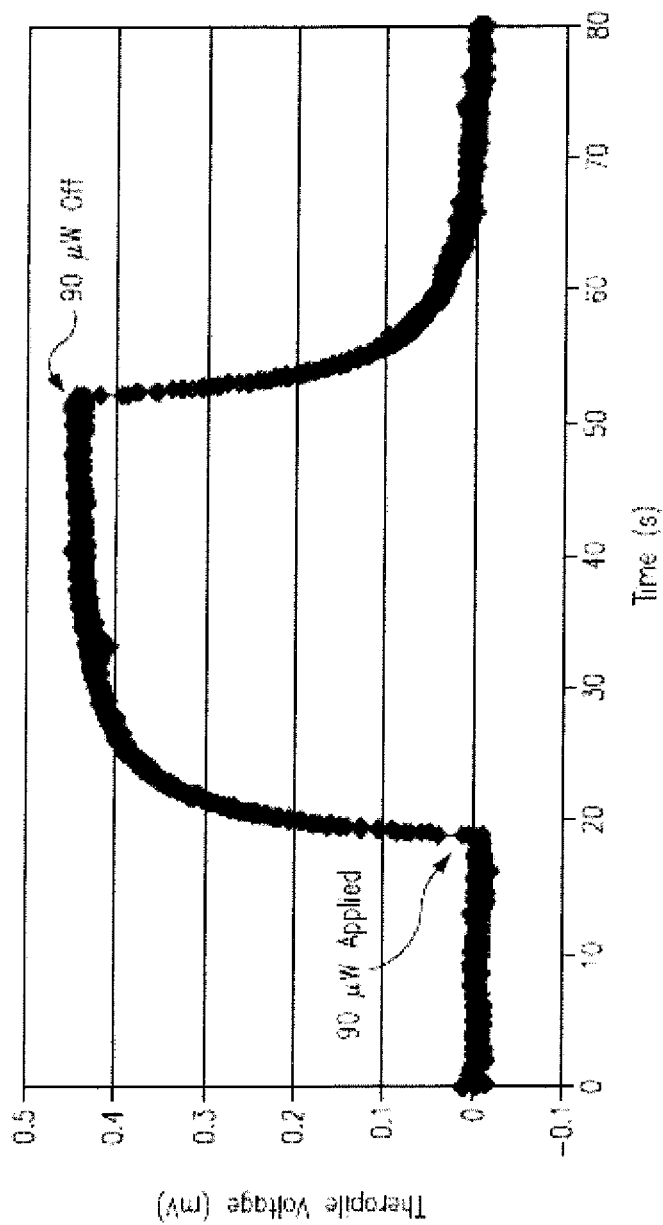
FIGS. 23a and 23b are plots showing calibration results of a microdevice according to some embodiments of the disclosed subject matter for performing isothermal titration calorimetry: transient response to a step differential power (23a), and steady-state response to a constant differential power (23b).
Figure 23B:
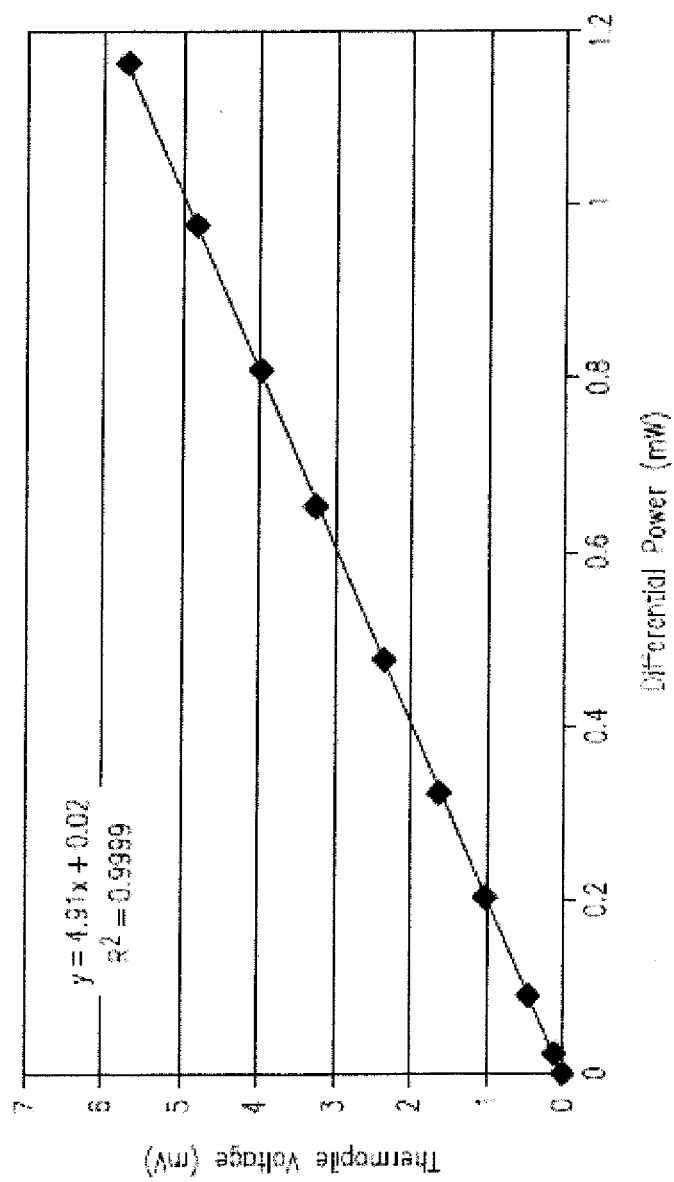

The MEMS-ITC device as schematically shown in FIG. 4 was used. Briefly, the device integrates two identical polydimethylsiloxane (PDMS) microchambers each (1 µL) situated on a freestanding polyimide thin film substrate and surrounded by air cavities for thermal isolation. The chambers are integrated with an antimony-bismuth (Sb—Bi) thermopile and connected to the inlets through an introduction channel which includes a passive chaotic mixer having herringbone-shaped ridges in the ceiling of a serpentine channel to generate a chaotic flow pattern that induces mixing of the incoming liquid streams. Some of the features of the MEMS-ITC device used were shown in FIG. 21. For ITC measurements, the two reactants, herein referred to as the ligand and sample for purpose of illustration, were introduced into the device and first mixed in the introduction channel, and then enter the sample calorimetric chamber, where the reaction is completed. In the meantime, the sample and pure buffer (devoid of the ligand) were also introduced into the device, becoming mixed before entering the reference calorimetric chamber. The differential temperature between the chambers were measured using the integrated thermopile, and was used to determine the thermal power from the reaction, from which the thermodynamic reaction parameters were calculated. The device was placed in a low-noise, temperature-controlled thermal enclosure (FIG. 22) where the thermopile output was measured. The sample and ligand were introduced using syringe pumps. Calibration experiments indicated that the device had a thermal time constant of 1.5 s with a linear steady-state thermal response (responsivity: 4.9 mV/mW) (FIG. 23).

C. ITC Measurement

Figure 24:
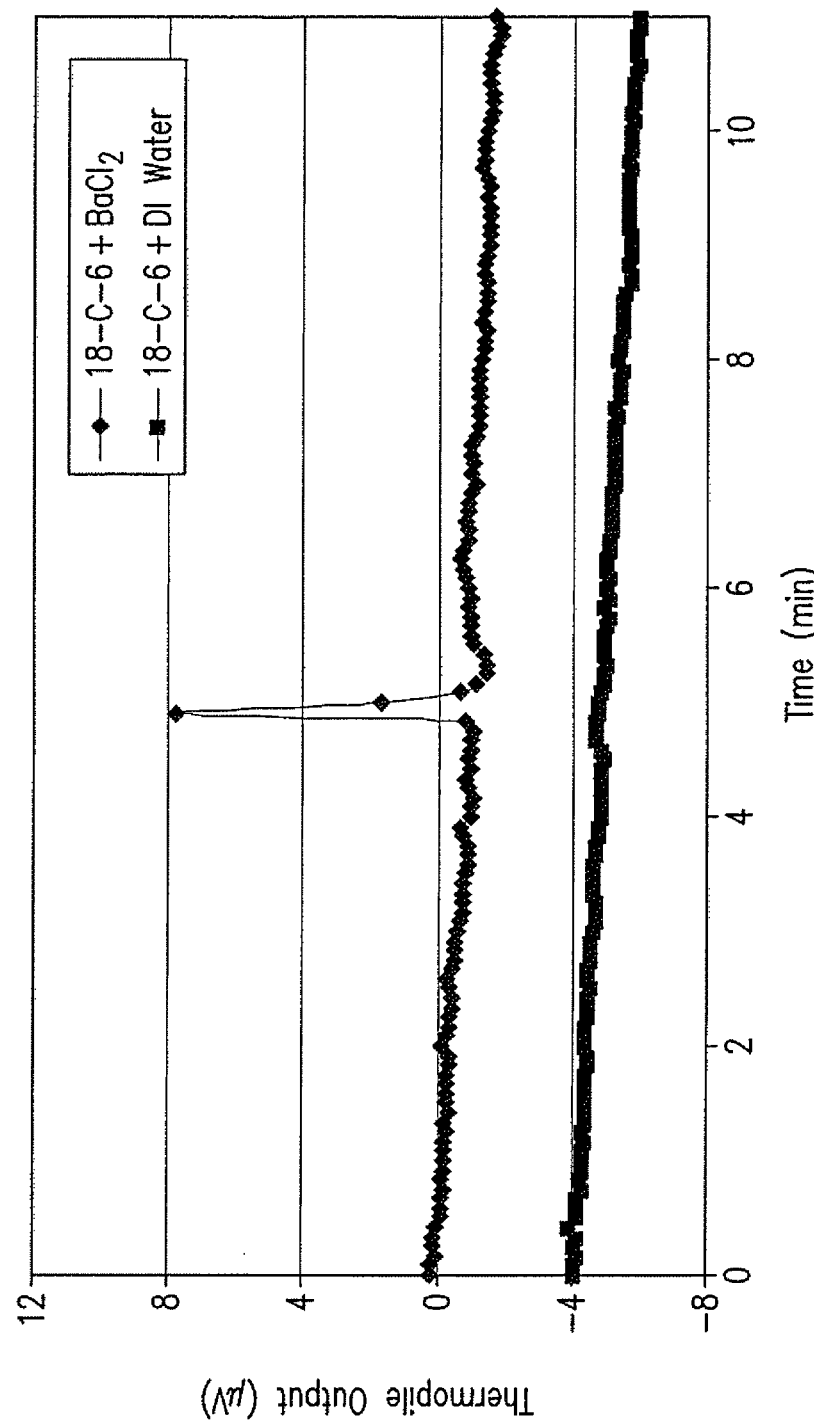
FIG. 24 is a plot showing a time-resolved output of a microdevice according to some embodiments of the disclosed subject matter upon introduction of 5 mM 18-C-6 and 4 mM $BaCl_2$ (each 0.5 µL), compared with measurement of 5 mM 18-C-6 titrated by DI water (plotted with a 4 µV offset for clarity).
Figure 25A:
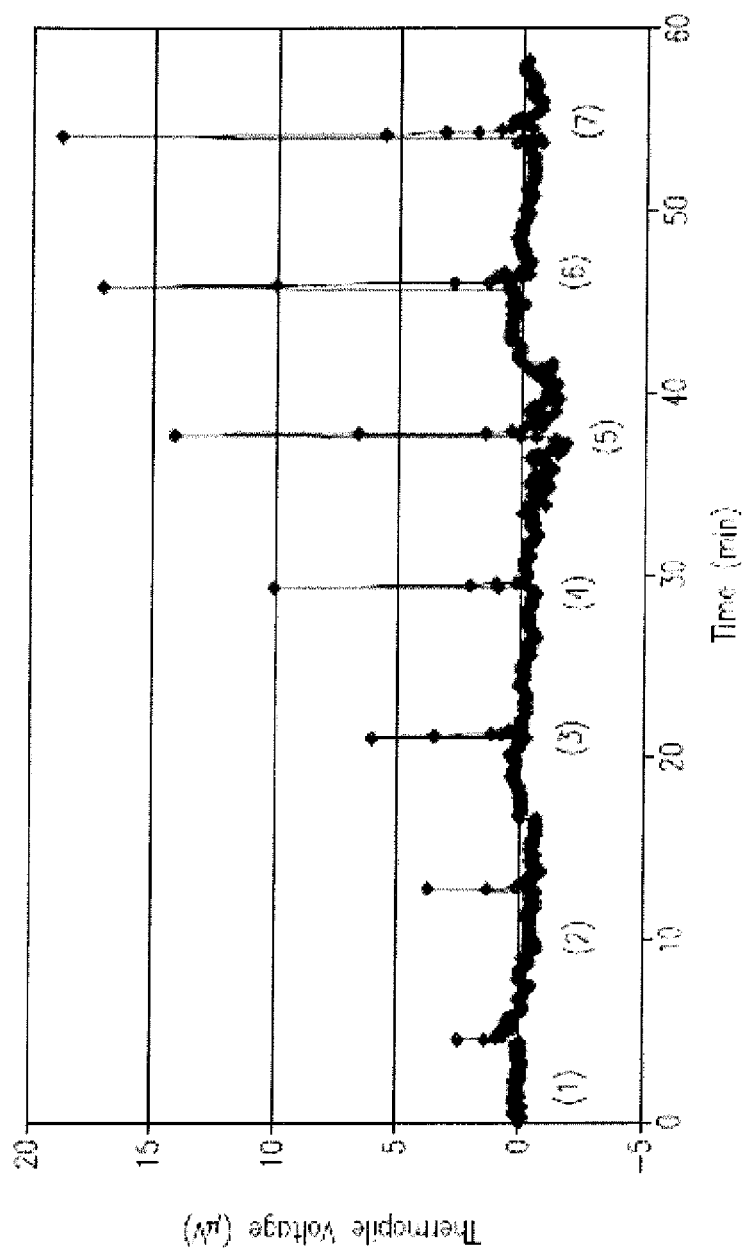
FIGS. 25a and 25b are plots for the output of a microdevice according to some embodiments of the disclosed subject matter in the isothermal titration calorimetric measurement of the binding of 5 mM 18-C-6 and $BaCl_2$ at continuous injections with a series of molar ratios (25a); and calculated heat of the binding of 18-C-6 and $BaCl_2$ as a function of molar ratio. The fitted curve is based on a one-site binding model.
Figure 25B:
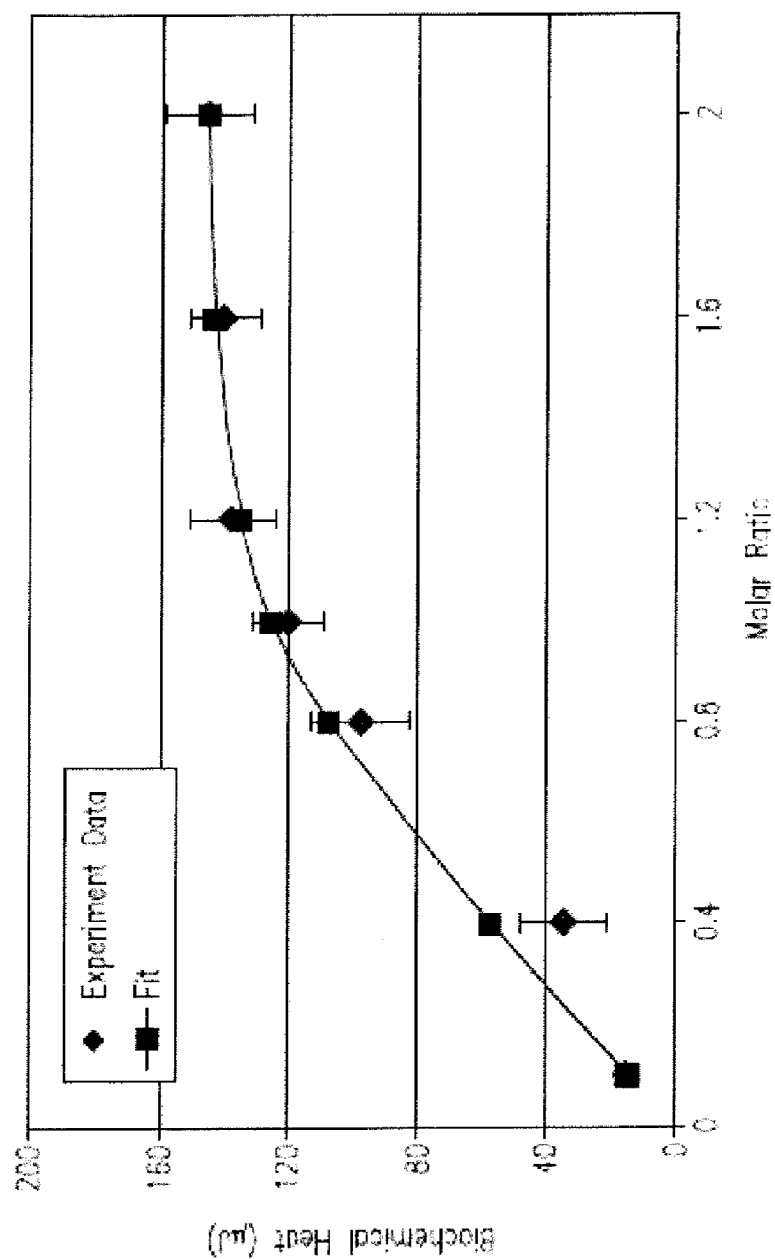
Figure 26:
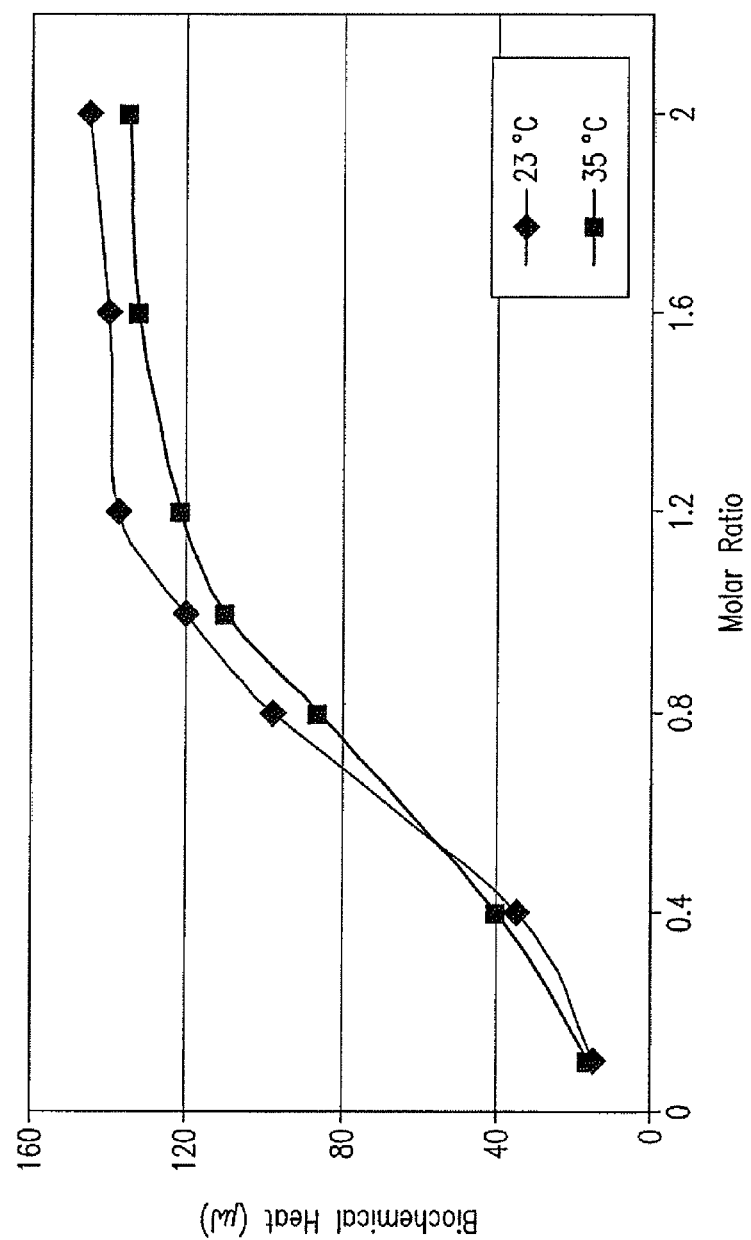
FIG. 26 is a plot showing the biochemical heat of binding of 18-C-6 and $BaCl_2$ as a function of molar ratio at temperatures of 23 and 35° C., as calculated from the output of a microdevice according to some embodiments of the disclosed subject matter.

The device was used for ITC measurements of a model reaction system consisting of 18-C-6 and $BaCl_2$. The time-resolved device output exhibited a reaction-specific spike (FIG. 24) upon introduction of 5 mM $BaCl_2$ and 4 mM 18-C-6 (each 0.5 µL) with no appreciable delay, indicating full mixing of the reactants. Using titrations with the molar ratio ($BaCl_2$/18-C-6) varying from 0.1 to 2 ((1) 0.1, (2) 0.4, (3) 0.8, (4) 1.0, (5) 1.2, (6) 1.6, (7) 2.0), the baseline-subtracted device output demonstrated spikes consistent with the titration reactions, and allowed construction of a binding isotherm (FIG. 25). ITC measurements were performed at 23 and 35° C. (FIG. 26), and the resulting isotherms were used to compute $K_B$ and $\Delta H$, which decrease with temperature (See Table 1 below). These results demonstrated that the MEMS-ITC device as disclosed affords detectable sample concentrations approaching those of conventional instruments (ca. 1 mM) with roughly three orders of magnitude reduction in volume.

TABLE 1

Temperature-dependent thermodynamic properties: the stoichiometry (N), binding affinity (KB) and enthalpy change (H), of the binding of 18-C-6 and BaCl2 at two temperatures

| Temperature (° C.) | N | $K_B(M^{-1})$ | $\Delta H(kJ/mol)$ |
|---|---|---|---|
| 23 | 1.0 | $6.0 \times 10^{-3}$ | 30.0 |
| 35 | 1.05 | $2.8 \times 10^{-3}$ | 27.8 |

Example 5

MEMS-Based Isothermal Calorimetry

Chaotic mixers and calorimetric chambers were fabricated in a single sheet using PDMS replica technique based on multiple-layered SU-8 molding. The microfabricated device integrated a 50-junction Sb—Bi thermopile and two 0.75 µL, calorimetric chambers with a center-to-center separation of 4 m. The calorimetric chambers had a cylindrical shape with a height of 150 µm and a diameter of 2.5 mm. The chaotic mixers were serpentine microchannels (width: 200 µm, height: 150 µm, length: approximately 15 mm) with herringbone-shaped ridges on the ceiling with each having a width of 40 µm, a height of 50 µm, an orientation angle of 60° to the channel sidewall, and an edge-to-edge distance between adjacent ridges of 30 µm. The nominal resistances of the integrated resistive microheaters and temperature sensors were 40 Ω and 55Ω, respectively.

To test the MEMS-IT device, a thermal enclosure was custom-built to house the device to shield the thermal disturbance from ambient, as well as provide uniform temperature control to the solutions loaded in the device. The thermal enclosure was improved with additional thermal isolation by suspending the sample stage from the base, vibration isolation by enhanced base mass and rubber buffering layer, and multiple-ports microfluidic feedthrough to the device. The temperature control of the thermal enclosure was implemented by a commercial temperature controller (Lakeshore Model 331). The device was first packaged with electrical interconnection wires and fluidic interconnection tubes before it was situated on the sample stage inside the thermal enclosure.

The on-chip microheaters, used for device calibration, were driven by a DC power supply (Agilent E3631A) and generated a constant differential heating power in the calorimetric chambers. The on-chip temperature sensors, used for in-situ temperature monitoring of the calorimetric chambers, were interrogated by a digital multimeter (Agilent 3410A). The thermopile output voltage, which is proportional to the differential temperature between the chambers, was measured by a nanovoltmeter (Agilent 34420A). The temperature monitoring of the calorimetric chambers and thermoelectric measurements were automated using a personal computer via a LabVIEW-based program. The biological sample and buffer solutions were degassed with a vacuum chamber built in-house, metered introduced into the MEMS-ITC device using a multiple-injections syringe pump (KD Scientific, KDS 220).

The device was first calibrated by measuring its steady-state and transient response to differential power generated by on-chip microheaters. Before ITC measurements, the baseline in device output, i.e., the thermopile output voltage in the absence of reaction, was measured with introduction of sample and buffer solutions to both calorimetric chambers. During ITC measurements, the thermal enclosure provided a controlled reaction temperature while the thermopile output, indicative of the differential bio-thermal power, was detected in real time, as well as the integrated micro-temperature sensor to monitor the temperatures of the calorimetric chambers. The volume of ligand and sample was fixed at 0.5 µL for each injection, while the molar ratio was adjusted by changing the concentration of ligand to be injected. The baseline in device output was always subtracted from the measurement signal for determination of thermodynamic properties of biomolecules.

The thermal time constant of the MEMS-ITC device was calibrated by applying a step differential power of 90 µW initially and then turned it off once the device output reached its equilibrium. The device output voltage was found to fit the first-order exponential growth and decay functions upon the application and removal of the differential power, respectively, from which the thermal time constant was determined to be approximately 1.5 s. In addition, the steady-state response of the device was calibrated to varying differential power, and a linear relationship showing a constant thermoelectric sensitivity of S=4.9 mV/mW was observed. The device's sensitivity was also calibrated at controller temperatures (provided by the thermal enclosure) from 20° C. to 45° C., and it was found that it remained almost unchanged with a relative standard deviation of less than 3%.

Figure 30:
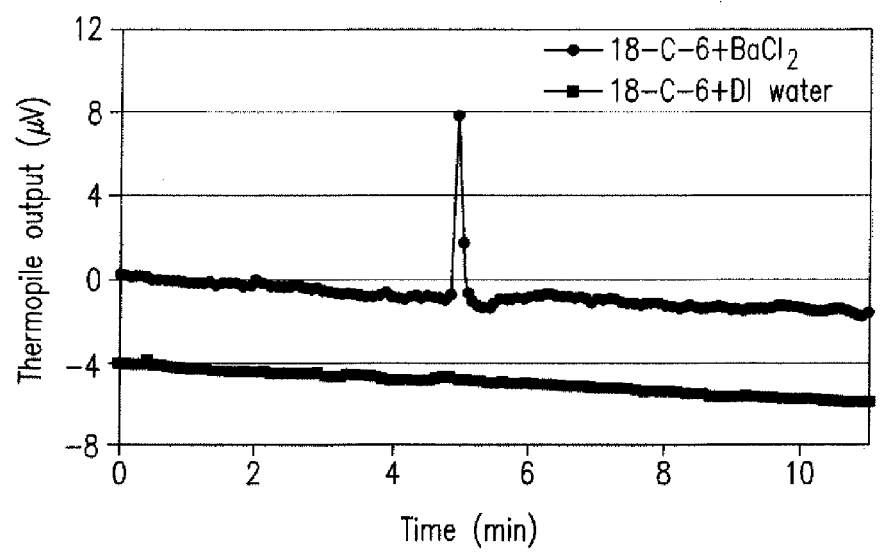
FIG. 30 illustrates a comparison of measurements of the time-resolved thermopile voltage upon introduction of 4 mM $BaCl_2$ and 5 mM 18-C-6 (each 0.5 µL) in the reaction chamber, and the signal upon introduction of sterile water and 5 mM 18-C-6 (also each 0.5 µL) in accordance with an embodiment of the disclosed subject matter.

The baseline stability and detection specificity was then tested using a standard chemical reaction of 18-Crown-6 (18-C-6) and barium chloride ($BaCl_2$) both prepared in sterile water (all chemicals from Sigma Aldrich). Using a flow rate of 50 μL/min, the solutions were injected into the calorimetric chambers within 1 s. Using a data acquisition rate of 2 $s^{-1}$ to monitor the device output in real time, no appreciable delay was observed after injection, indicating full mixing of the reactants. A comparison of the time-resolved thermopile voltage upon introduction of 4 mM $BaCl_2$ and 5 mM 18-C-6 (each 0.5 μL) in the reaction chamber, and the signal upon introduction of sterile water and 5 mM 18-C-6 (also each 0.5 μL) is shown in FIG. 30. For both measurements, the reference chamber was injected with sterile water and 5 mM 18-C-6, and a data acquisition rate of 0.2 $s^{-1}$ was used due to instrument configuration for lower background noise. The device exhibited a stable baseline throughout the measurements and a reaction-specific spike attributable to the exothermic nature of the binding between 18-C-6 and $BaCl_2$. The reaction completed in approximately 20-30 s, during which any interference from solution injection and mixing were generally negligible.

Figure 31:
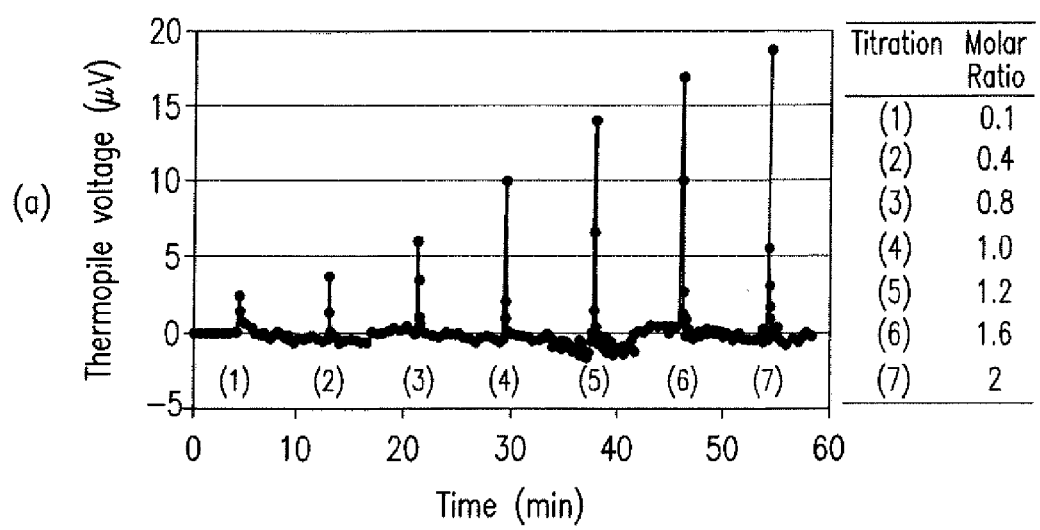
FIG. 31 illustrates the baseline-subtracted device output of a device for characterizing biochemical reactions in accordance with one embodiment of the disclosed subject matter.

The MEMS-ITC device was then used to characterize biomolecular interactions. The $BaCl_2$-18-C-6 reaction was used to validate the ITC measurements. By varying the molar mass ration ($MBACl_2$/M18-C-6) from 0.1 to 2, the baseline-subtracted device output demonstrated spikes consistent with the titration reactions. The baseline-subtracted device output is shown in FIG. 31. Rather than measuring the heat evolved with the addition of several aliquots of $BaCl_2$ to a single sample of 18-C-6 as performed in commercial ITC instruments, the ITC experiment was performed at discrete measurements each with a definite concentration of $BaCl_2$ (0.5-10 mM) and a fixed concentration of 18-C-6 (5 mM). Each measurement was completed in approximately 5 min.

The thermopile voltage was the used to calculate the bio-thermal power based on Equation 1. The bio-thermal power was then used to calculate the reaction heat by integral of the biothermal power during the process.

Figure 32:
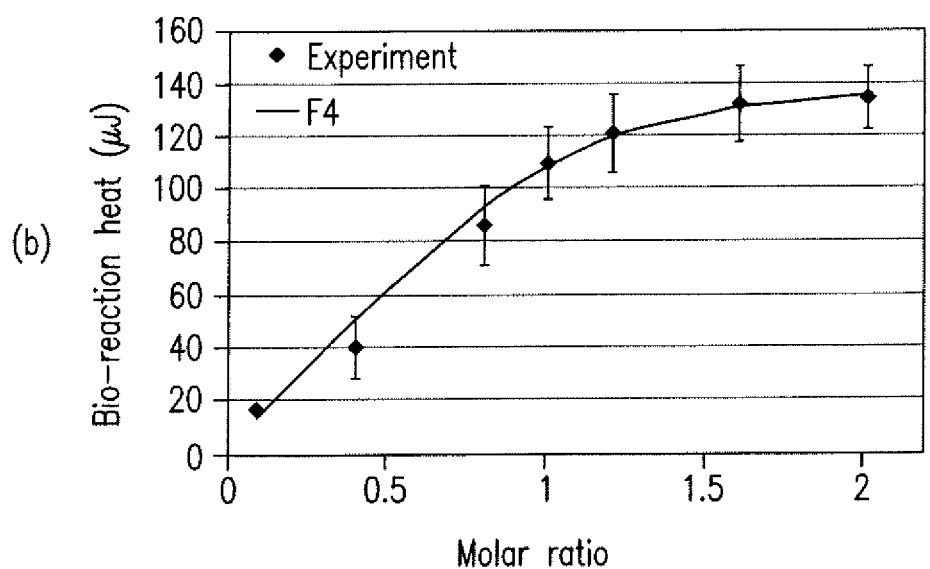
FIG. 32 illustrates the calculated reaction heat derived from the output voltage measurements in accordance with one embodiment of the disclosed subject matter.

The binding isotherm of the reaction of 18-C-6 and $BaCl_2$, as well as the fitted curve, is shown in FIG. 32, with error bars representing the standard deviation from three measurements a each molar ratio. Note that for this specific BaCl2-18-C-6 system, the device affords detectable sample concentrations approaching those of convention instruments (ca. 1 mM) with roughly three orders of magnitude reduction in volume.

ITC measurements were performed of the biological reaction of 18-C-6 and BaCl2 at controlled temperatures of 23° C. and 35° C., and the resulting binding isotherms were used to compute the temperature-dependent thermodynamic properties of N, $K_B$, and ΔH. In particular, as temperature increases from 23° C. to 35° C., N slightly increases from 1.00 to 1.05, while $K_B$ decreases from approximately 6.0× $10^{-3}$ to 2.0×$10^{-3}$ $M^{-1}$ and ΔH decreases from 30.0 o 27.8 kJ/mol, showing a trend of slightly weaker binding with temperature. These properties and their temperature dependence obtained by suitable measurements agree reasonably with published data using commercial calorimeters as shown in FIG. 33.

Figure 34:
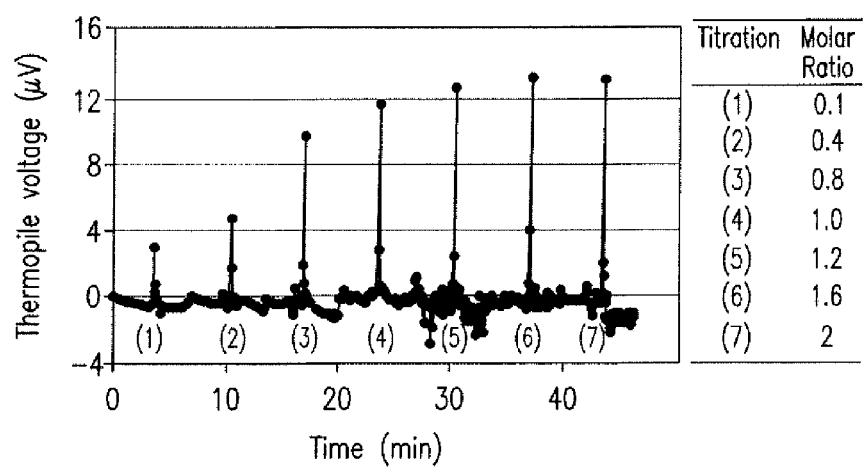
FIG. 34 illustrates device output exhibited titration-dependent spikes in correspondence to the molar ratio at varying molar ratios in accordance with an embodiment of the disclosed subject matter.

The MEMS-ITC device was further applied for characterization of biomolecular interactions, e.g., ligand-protein binding, using a demonstrative system of cytidine 2'-monophosphate (2'CMP) and ribonuclease A (RNase A). 2'CMP is known as a strong inhibitor of substrates that bind to the active site of RNase A. Both reagents were prepared in 50 mM potassium acetate buffer, pH 5.5. Similarly, at varying molar rations (2'CMP/RNase A) from 0.1 to 2, the device output exhibited titration-dependent spikes in correspondence to the molar ratio as shown in FIG. 34. ITC measurements of 2'CMP-RNase A binding at controlled temperatures of 23° C. and 35° C. with error bars from three measurements at each molar ration were also performed. In turn, the temperature-dependent thermodynamic properties associated with this biomolecular interaction were determined from fitting the experimental data to the described model in Equation 3. The results again agreed reasonably with published data using commercial ITC instruments as shown in FIG. 35. For 2'CMP-RNase A interaction, the reasonably detectable concentration of RNase A can be as low as 2 mM. These results demonstrate the utility of this MEMS-ITC device for efficient characterization of a wide variety of biomolecular interactions.

The description herein merely illustrates the principles of the disclosed subject matter. Various modifications and alterations to the described embodiments will be apparent to those skilled in the art in view of the teachings herein. Further, it should be noted that the language used herein has been principally selected for readability and instructional purposes, and can not have been selected to delineate or circumscribe the inventive subject matter. Accordingly, the disclosure herein is intended to be illustrative, but not limiting, of the scope of the disclosed subject matter.

The invention claimed is:

1. A microdevice for calorimetric measurement, comprising:
    a first thermally isolated microchamber comprising a first serpentine structure, and
    a second thermally isolated microchamber comprising a second serpentine structure, each of the first and second serpentine structures have a plurality of long serpentine edges and a plurality of short serpentine edges;
    a thin film substrate;
    wherein the first thermally isolated microchamber and the second thermally isolated microchamber are each supported on the thin film substrate,
    wherein the thin film substrate has a first side constituting a floor of the first and second thermally isolated microchambers and a second side opposing the first side, and
    wherein the thin film substrate comprises a thermoelectric sensor, the thermoelectric sensor configured as a thin layer thermopile comprising a plurality of adjacent segments of dissimilar materials, each of the adjacent segments joined together at opposite ends forming a plurality of thermocouple junctions, the thermocouple junctions oriented serially along the long serpentine edges of the first and second serpentine structures of the first and second thermally isolated microchambers, the thermocouple junctions disposed under each of the first and second thermally isolated microchambers and configured to measure the temperature differential between the first and second thermally isolated microchambers.

2. The microdevice of claim 1, wherein a thermoelectric sensitivity per thermocouple is greater than 80 µV/° C.).

3. The microdevice of claim 1, where the dissimilar thermoelectric materials comprise n-type and p-type bismuth telluride, and n-type and p-type antimony telluride.

4. The microdevice of claim 1, wherein the dissimilar materials comprise antimony and bismuth.

5. The microdevice of claim 1, wherein the material of the polymeric diaphragm has a tensile strength of greater than 55 MPa or Young's Modulus greater than 500 MPa.

6. The microdevice of claim 1, wherein the material for the polymeric diaphragm is selected from polyimide, parylene, polyester, and polytetrafluoroethylene.

7. The microdevice of claim 1, wherein the thin film substrate further comprises: a first microheater and a first temperature sensor, each aligned under the first thermally isolated microchamber; and a second microheater and a second temperature sensor, each aligned under the second thermally isolated microchamber.

8. The microdevice of claim 7, wherein the thermocouple junctions of the thermoelectric sensor are located near the center of the long serpentine edges of each of the first and second serpentine structures, and vertically aligned with the first temperature sensor and the second temperature sensor, respectively.

9. The microdevice of claim 7, wherein the thermopile is located in a different horizontal plane than and insulated from each of the first and second microheaters and the first and second temperature sensors.

10. The microdevice of claim 7, wherein each of the first microheater, the first temperature sensor, the second microheater, and the second temperature sensor is in a form of a thin layer of deposited metal/alloy or metals/alloys impregnated in the thin film substrate.

11. The microdevice of claim 10, wherein each of the first and second microheaters are patterned to provide uniform heating in each of the first and second thermally isolated microchambers.

12. The microdevice of claim 1, wherein each of the first thermally isolated microchamber and the second thermally isolated microchamber is defined by a surrounding wall made from polydimethylsiloxane (PDMS).

13. The microdevice of claim 1, wherein the thin film substrate includes a top layer contacting each of the first thermally isolated microchamber and the second thermally isolated microchamber, the top layer made from a mixture of PDMS and the material from which the polymeric diaphragm is made.

14. The microdevice of claim 1, further comprising a silicon wafer substrate contacting the second side of the thin film substrate.

15. The microdevice of claim 14, wherein the area on the second side of the thin film substrate corresponding to a cross section of each of the first and second thermally isolated microchambers does not contact any other material except air.

16. The microdevice of claim 1, further including a first introduction channel and a second introduction channel, each configured to provide passive chaotic mixing for a solution flowing through the first or the second introduction channel.

17. The microdevice of claim 16, wherein each of the first introduction channel and a second introduction channel comprises a portion having a serpentine shape.

18. The microdevice of claim 16, wherein each of the first introduction channel and a second introduction channel comprises internal ridges configured to create turbulence in the solution flowing through the first or the second introduction channel.

19. The microdevice of claim 1, further comprising a thermal enclosure enclosing the microdevice.

20. The microdevice of claim 19, wherein the thermal enclosure comprises two or more metal enclosures.

21. The microdevice of claim 19, wherein the microdevice is positioned on a metal stage of the thermal enclosure.

22. The microdevice of claim 19, wherein the thermal enclosure comprises one or more heaters.

23. The microdevice of claim 22, wherein the one or more heaters comprise Peltier heaters.

24. The microdevice of claim 22, wherein the thermal enclosure comprises a controller to adjust a voltage applied to the one or more heaters.

25. The microdevice of claim 19, wherein the thermal enclosure comprises a heat sink.

26. A method of determining a thermal property of an analyte, comprising:
providing a microdevice, comprising:
a first thermally isolated microchamber comprising a first serpentine structure, and
a second thermally isolated microchamber comprising a second serpentine structure, each of the first and second serpentine structures have a plurality of long serpentine edges and a plurality of short serpentine edges;
a thin film substrate;
wherein the first thermally isolated microchamber and the second thermally isolated microchamber are each supported on the thin film substrate,
wherein the thin film substrate has a first side constituting a floor of the first and second thermally isolated microchambers and a second side opposing the first side,
wherein the thin film substrate comprises:
a thermoelectric sensor, the thermoelectric sensor configured as a thin layer thermopile comprising a plurality of adjacent segments of dissimilar materials, each of the adjacent segments joined together at opposite ends forming a plurality of thermocouple junctions, the thermocouple junctions oriented serially along the long serpentine edges of the first and second serpentine structures of the first and second thermally isolated microchambers, the thermocouple junctions disposed under each of the first and second thermally isolated microchambers and configured to measure the temperature differential between the first and second thermally isolated microchambers;
a first microheater and a first temperature sensor, each aligned under the first thermally isolated microchamber; and
a second microheater and a second temperature sensor, each aligned under the second thermally isolated microchamber;
providing a thermal enclosure enclosing the microdevice;
loading a sample material containing an analyte into the first thermally isolated microchamber;
loading a reference material into the second thermally isolated microchamber, the reference material does not contain the analyte;
heating the thermal enclosure at a predetermined temperature scanning rate;

determining a thermal property of the analyte based on the measured temperature differential between the first thermally isolated microchamber and the second thermally isolated microchamber.

27. The method of claim 26, further comprising providing a temporally periodic variation in the heating power during the heating of the thermal enclosure.

28. The method of claim 27, wherein providing the temporally periodic variation in the heating power comprises providing identically temporally modulated heating to the sample material and the reference material by the first microheater and the second microheater of the microdevice.

29. The method of claim 28, wherein the temporally modulated heating is controlled by a waveform generator.

30. The method of claim 28, further comprising calibrating the output of the thermoelectric sensor under a plurality of modulation frequencies.

31. The method of claim 26, further comprising calibrating the output of the thermoelectric sensor using the first or the second microheater of the microdevice that is aligned underneath the first thermally isolated microchamber to provide a constant differential heating power between the first microchamber and the second microchamber.

32. The method of claim 26, wherein the analyte is a biomolecule.

33. The method of claim 32, wherein the thermal property of the biomolecules is a thermal property associated with the denaturing of the biomolecules.

34. A method of determining a thermal property of an analyte, comprising
providing a microdevice including two thermally isolated microchambers, each of the two thermally isolated microchambers comprising a serpentine structure, the serpentine structure having a plurality of long serpentine edges and a plurality of short serpentine edges. and being supported on a thin film substrate, wherein the thin film substrate comprises a thermoelectric sensor configured to measure the temperature differential between the first and second thermally isolated microchambers, the thermoelectric sensor configured as a thin layer thermopile comprising a plurality of adjacent segments of dissimilar materials, each of the adjacent segments joined together at opposite ends forming a plurality of thermocouple junctions, the thermocouple junctions oriented serially along the long serpentine edges serpentine structure;
providing a thermal enclosure enclosing the microdevice;
loading a sample material containing an analyte into one of the two thermally isolated microchambers;
loading a reference material into the other of the two thermally isolated microchambers, the reference material does not contain the analyte;
heating the thermal enclosure at a predetermined temperature scanning rate;
providing additional temporally modulated heating to the sample material and the reference material during the heating of the thermal enclosure; and
determining a thermal property of the analyte based on the measured temperature differential between the two thermally isolated microchambers.

35. The method of claim 34, wherein the microdevice further comprises a first microheater and a first temperature sensor, each aligned under one of the two thermally isolated microchambers, and a second microheater and a second temperature sensor, each aligned under the other of the two thermally isolated microchambers, the method further comprising calibrating the output of the thermoelectric sensor using the first microheater of the microdevice to provide a constant differential heating power between the two thermally isolated microchambers.

36. A method of determining heat involved in a reaction between at least two substances, comprising:
providing a microdevice, comprising:
a first thermally isolated microchamber comprising a first serpentine structure and
a second thermally isolated microchamber comprising a second serpentine structure each of the first and second serpentine structures have a plurality of long serpentine edges and a plurality of short serpentine edges;
a thin film substrate;
wherein the first thermally isolated microchamber and the second thermally isolated microchamber are identical in volume and configuration, and arranged side by side, each supported on the thin film substrate,
wherein the thin film substrate has a first side constituting a floor of the first and second microchambers and a second side opposing the first side, and
wherein the thin film substrate comprises a thermoelectric sensor, the thermoelectric sensor configured as a thin layer thermopile comprising a plurality of adjacent segments of dissimilar materials, each of the adjacent segments joined together at opposite ends forming a plurality of thermocouple junctions, the thermocouple junctions oriented serially along the long serpentine edges of the first and second serpentine structures of the first and second thermally isolated microchambers, the thermocouple junctions disposed under each of the first and second thermally isolated microchambers and configured to measure the temperature differential between the first and second thermally isolated microchambers;
providing a thermal enclosure enclosing the microdevice;
providing a sample solution into the first thermally isolated microchamber, the sample solution containing a mixture of a first substance and a second substance at a first concentration ratio;
providing a reference solution into the second thermally isolated microchamber, the reference solution does not contain at least one of the first and the second substances;
maintaining the thermal enclosure at a first predetermined constant temperature;
determining the heat involved in the reaction between the first substance and the second substance at the first ratio and the first predetermined constant temperature based on the measured temperature differential between the first microchamber and the second microchamber.

37. The method of claim 36, wherein the reaction between the first and second substances is a chemical reaction or a physical binding.

38. The method of claim 36, wherein the reaction between the first and second substances is ligand-protein binding.

39. The method of claim 36, further comprising providing the first and the second substances in the sample solution at a second concentration ratio different from the first concentration ratio, and determining the heat involved in the reaction between the first and the second substances at the second concentration ratio.

40. The method of claim 36, further comprising maintaining the thermal enclosure at a second predetermined constant temperature different from the first predetermined constant temperature, and determining the heat involved in the reaction between the first and the second substances at the second predetermined constant temperature.

41. The method of claim 36, wherein the microdevice further comprises a first introduction channel and a second introduction channel, the first introduction channel having at least two inlets; and wherein feeding the sample solution into first thermally isolated microchamber comprises feeding two solutions containing the first substance and the second substance into the at least two inlets of the first introduction channel, respectively, and allowing the sample solution to flow into the first thermally isolated microchamber through the first introduction channel.

42. The method of claim 41, wherein the first introduction channel comprises a portion having a serpentine shape.

43. The method of claim 41, wherein the first introduction channel comprises internal ridges configured to create turbulence in a solution flowing through the first introduction channel.

44. A method of determining heat involved in a reaction between at least two substances, comprising:
    providing a microdevice including a first thermally isolated microchamber comprising a first serpentine structure and a second thermally isolated microchamber comprising a serpentine structure, each of the first and second serpentine structures have a plurality of long serpentine edges and a plurality of short serpentine edges, and each of the first and second thermally isolated microchambers supported on a thin film substrate, wherein the thin film substrate comprises a thermoelectric sensor configured to measure the temperature differential between the first and second thermally isolated microchambers, the thermoelectric sensor configured as a thin layer thermopile comprising a plurality of adjacent segments of dissimilar materials, each of the adjacent segments joined together at opposite ends forming a plurality of thermocouple junctions, the thermocouple junctions oriented serially along the long serpentine edges of the first and second serpentine structures of the first and second thermally isolated microchambers;
    providing a thermal enclosure enclosing the microdevice;
    feeding a sample solution into the first thermally isolated microchamber, wherein the sample solution is prepared mixing a first substance with a second substance;
    feeding a reference solution into the second thermally isolated microchamber, the reference solution does not contain at least one of the first and the second substances;
    determining the heat involved in the reaction between the first substance and the second substance based on the measured temperature differential between the first microchamber and the second microchamber.

* * * * *